US005750669A

United States Patent [19]
Rösch et al.

[11] Patent Number: 5,750,669
[45] Date of Patent: May 12, 1998

[54] OLIGONUCLEOTIDE ANALOGS WITH TERMINAL 3'-3' OR 5'-5' INTERNUCLEOTIDE LINKAGES

[75] Inventors: Hannelore Rösch, Ulm; Anja Fröhlich, Illerkirchberg; Jose Flavio Ramalho-Ortigao, Ulm; Matthias Montenarh, Senden-Ay; Hartmut Seliger, Elchingen-Thalfingen, all of Germany

[73] Assignee: Hoechst Aktiengesellschaft, Frankfurt am Main, Germany

[21] Appl. No.: 282,503

[22] Filed: Aug. 1, 1994

Related U.S. Application Data

[63] Continuation of Ser. No. 723,440, Jun. 28, 1991, abandoned.

[30] Foreign Application Priority Data

Jul. 2, 1990 [DE] Germany .................... 40 21 019.7

[51] Int. Cl.$^6$ .................................................. C07H 21/04
[52] U.S. Cl. ................. 536/24.3; 536/23.1; 536/24.5; 435/6; 514/44
[58] Field of Search ................. 536/24.5, 24.3, 536/23.1; 514/44; 435/6

[56] References Cited

U.S. PATENT DOCUMENTS

| 4,123,610 | 10/1978 | Summerton et al. | 514/44 |
| 4,711,955 | 12/1987 | Ward et al. | 536/24.3 |
| 4,795,700 | 1/1989 | Dervan et al. | 435/5 |
| 4,835,263 | 5/1989 | Nguyen et al. | 536/24.3 |

FOREIGN PATENT DOCUMENTS

| 0136543 | 4/1985 | European Pat. Off. |
| 8909221 | 10/1989 | WIPO |
| 9012022 | 10/1990 | WIPO |

OTHER PUBLICATIONS

Krieg et al., "CpG Motifs in Bacterial DNA Trigger Direct B–Cell Activation," *Nature*, 374, 546–549 (6 Apr. 1995).

M. Ratajczak, et al., "In Vivo Treatment of Human Leukemia in a Scid Mouse Model with c–myb Antisense Oligodeoxynucleotides", Dec. 1992, Proc. Natl. Acad. Sci. USA, vol. 89, pp. 11823–11827.

G. Gray, et al., "Antisense DNA Inhibition of Tumor Growth Induced by c–Ha–ras Oncogene in Nude Mice", Feb. 1993, Cancer Research, pp. 577–580.

Osen–Sand, et al., "Inhibition of Axonal Growth by SNAP–25 Antisense Oligonucleotides in vitro and in vivo", Nature, Jul. 1993, vol. 364, pp. 445–448.

Higgins, et al., "Antisense Inhibition of the p65 Subunit of NF–kB Blocks Tumorigenicity and Causes Tumor Regression", Proc. Natl. Acad. Sci. USA, Nov. 1993, vol. 90, pp. 9901–9905.

Dean, et al., "Inhibition of Protein Kinase C–α Expression in Human A549 Cells by Antisense Oligonucleotides Inhibits Induction of Intercellular Adhesion Molecule 1 (ICAM–1) mRNA by Phorbol Esters", Journ. of Biological Chemistry, Jun. 1994, vol. 269, No. 23, pp. 16416–16424.

Shi, et al., "Transcatheter Delivery of c–myc Antisense Oligomers Reduces Neointimal Formation in a Porcine Model of Coronary Artery Balloon Injury", Aug. 1994, Basic Science Reports, vol. 90, No. 2, pp. 944–951.

Dean, et al., "Inhibition of Protein Kinase C–α Expression in Mice After Systemic Administration of Phosphorothioate Antisense Oligodeoxynucleotides", Nov. 1994, Proc. Natl. Acad. Sci. USA, vol. 91, pp. 11762–11766.

Gillardon, et al., "Expression of C–Fos and C–Jun in the Cornea, Lens, and Retina After Ultraviolet Irradiation of the Rat Eye and Effects of Topical Antisense Oligodeoxynucleotides", British Journ. of Ophthalmology, 1995, vol. 79, pp. 277–281.

Gillardon, et al., "Inhibition of C–Fos Expression in the UV–irradiated Epidermis by Topical Application of Antisense Oligodeoxynucleotides Suppresses Activation of Proliferating Cell Nuclear Antigen", Carcinogenesis, 1995, vol. 16, No. 8, pp. 1853–1856.

Field, et al., "Antisense Oligonucleotides: Rational Drug Design for Genetic Pharmacology", Exp. Opin. Invest. Drugs, 1995, vol. 4, No. 9, pp. 799–821.

Skutella, et al., "Antisense Oligodeoxynucleotides for In Vivo Targeting of Corticotropin–Releasing Hormone mRNA: Comparison of Phosphorothioate and 3'–Inverted Probe Performance," Horm. metab. Res., vol. 26, 1994, pp. 460–464.

Gillardon, et al., "Activation of c–Fos contributes to amyloidβ–peptide–induced neurotoxicity," Brain Research, 1996, vol. 706, pp. 169–172.

Knorre et al., "Oligonucleotides Linked to Reactive Groups," Ch. 8 in *Oligonucleotides–Inhibitors of Gene Expression*, Cohen (ed.), CRC Press, Boca Raton, FL, 1989, pp. 173–196.

Héléne et al., "Control of Gene Expression by Oligonucleotides Covalently Linked to Intercalating Agents and Nucleic–Acid Cleaving Reagents," Ch. 7 in *Oligonucleotides–Inhibitors of Gene Expression*, Cohen (ed.), CRC Press, Boca Raton, FL, 1989, pp. 137–172.

François et al., "Periodic Cleavage of Poly(dA) by Oligothymidylates Covalently Linked to the 1,10–Phenanthroline–Copper Complex," Biochemistry, 27(7), 2272–2276 (1988).

Praseuth et al., "Sequence–Targeted Photosensitized Reactions in Nucleic Acids by Olig–α–deoxynucleotides and Oligo–β–deoxynucleotides Covalently Linked to Proflavin," Biochemistry, 27(8), 3031–3038 (1988).

(List continued on next page.)

*Primary Examiner*—John Kight
*Assistant Examiner*—L. Eric Crane
*Attorney, Agent, or Firm*—Finnegan, Henderson, Farabow, Garrett & Dunner, L.L.P.

[57] ABSTRACT

Therapeutically utilizable oligonucleotides of the formulae I and II have been obtained by introduction of terminal 3'—3' and 5'—5' linkages. These compounds are stable to nucleases and suppress the biological function of nucleic acids.

10 Claims, 6 Drawing Sheets

Doan et al., "Sequence–Targeted Chemical Modification of Nucleic Acids by Complementary Oligonucleotides Covalently Linked to Porphyrins," *Nucleic Acids Research*, 15(21), 8643–8659 (1987).

Asseline et al., "Oligodeoxynucleotides Covalently Linked to Intercalating Dyes as Base–Specific Ligands. Influence of Dye Attachment Site," *The EMBO Journal*, 3(4), 795–800 (1984).

Chu et al., "Nonenzymatic Sequence–Specific Cleavage of Single–Stranded DNA," *Proc. Nat. Acad. Sci. USA*, 82(Feb), 963–967 (1985).

van der Krol et al., "Modulation of Eukaryotic Gene Expression by Complementary RNA or DNA Sequences," *BioTechniques*, 6(10), 958–976 (1988).

Thuong et al., "Chemical Synthesis of Natural and Modified Oligodeoxynucleotides," *Biochemie*, 67, 673–684 (1985).

Zon, "Pharmaceutical Considerations," Ch. 11 in in *Oligonucleotides—Inhibitors of Gene Expression*, Cohen (ed.), CRC Press, Boca Raton, FL, 1989, pp. 233–247.

Gura, "Antisense Has Growing Pains—Efforts to Develop Antisense Compounds for Cancer, AIDS, and Other Diseases Have Encountered Some Unexpected Questions About How the Drugs Really Work," *Science*, 270, 575–577 (1995).

Gutai et al.(I), "Evolutionary Variants of Simarian Virus 40: Nucleotide Sequence of a Conserved SV40 DNA Segment Containing the Origin of Viral DNA Replication as an Inverted Repetition," *J. Mol. Biol.*, 126, 259–274 (1978).

Gutai et al.(II), "Evolutionary Variants of Simarian Virus 40: Cellular DNA Sequences and Sequences at Recombinant Joints of Substituted Variants," *J. Mol. Biol.*, 126, 275–288 (1978).

Fiers, "Complete Nucleotide Sequence of SV 40 DNA," *Nature*, 273, 113–120 (1978).

Tenen et al., "Binding of Simian Virus 40 Large T Antigen from Virus–infected Monkey cells to Wild–type and Mutant Viral Replication Origins," *J. Mol. Biol.*, 168, 791–808 (1983).

Everett et al., "The Repeated GC–rich Motifs Upstream from the TATA Box are Important Elements of the SV 40 Early Promoter," *Nucleic Acids Resrarch*, 11(8), 2447–2464 (1983).

Renkawitz et al., "Sequences in the Promoter Region of the Chicken Lysozyme Gene Required for Steriod Regulation and Receptor Binding," *Cell*, 37, 503–510 (1984).

Subramanian et al., "The Primary Structure of Regions of the SV 40 DNA Encoding Ends of mRNA," in *Prog. Nucleic Acid Res. Mol. Biol.*, vol. 19, Cohn et al. eds., Academic Press, 1976, see pp. 157–164.

Wakamiya et al., "Structure of Simian Virus 40 Recombinants That Contain both Host and Viral DNA Sequences, " *J. Biol. Chem.*, 254(9), 3584–3591 (1979).

Goodchild, "Inhibition of Gene Expression by Oligonucleotides,"in *Oligodeoxynucleotides[:] Antisense Inhibitors of Gene Expression*, J. S. Cohen (ed.), CRC Press, Inc., Boca Raton, FL, 1989, see pp. 53–77.

R. S. Root–Bernstein(I), "AIDS IS More Than HIV: Part I," *Genetic Engineering News*, Sep. 1, 1992, pp. 4–6.

R. S. Root–Bernstein(II), "AIDS IS More Than HIV: Part II," *Genetic Engineering News*, Sep. 15, 1992, pp. 4–5.

Hood et al., *Immunology, 2nd Ed.*, Bemjamin/Cummings Publishing Co., Menlo Park, CA, 1984, p. 501.

Offensperger et al., "In vivo Inhibition of Duck Hepatitis B Virus Replication and Gene Expression by Phosphorothioate Modified Antisense Oligodeoxynucleotides," *EMBO Journal*, 12(3), 1257–1262 (1993).

Wahlestedt et al., "Modulation of Anxiety and Neuropeptide Y–Y1 Receptors by Antisense Oligodeoxynucleotides," *Science*, 259, 528–531(1993).

Seliger et al., "Oligonucleotide Analogs with Dialkyl Silyl Internucleotide Linkages," *Nucleoside & Nucleotides*, 6(1–2), 483–484 (1987).

Sonveaux, "The Organic Chemistry Underlying DNA Synthesis," *Bioorganic Chemistry*, 14, 274–325 (1986).

Caruthers, "Synthesis of Oligonucleotides and Oligonucleotide Analogues," Ch. 1 in *Oligodeoxynucleotides[:] Antisense Inhibitors of Gene Expression*, J. S. Cohen (ed.), CRC Press, Inc., Boca Raton, FL, 1989, see pp. 7–24.

Cohen, "Introduction: Strategies and Realities," Introduction in *Oligodeoxynucleotides[:] Antisense Inhibitors of Gene Expression*, J. S. Cohen (ed.), CRC Press, Inc., Boca Raton, FL, 1989, see pp. 1–6.

Stein et al., "Phosphorothioate Oligodeoxynucleotide Analogues," Ch. 5 in *Oligodeoxynucleotides[:] Antisense Inhibitors of Gene Expression*, J. S. Cohen (ed.), CRC Press, Inc., Boca Raton, FL, 1989, see pp. 97–117.

Miller, "Non–ionic Antisense Oligonucleotides," Ch. 4 in *Oligodeoxynucleotides[:] Antisense Inhibitors of Gene Expression*, J. S. Cohen (ed.), CRC Press, Inc., Boca Raton, FL, 1989, see pp. 79–95.

Rayner et al., α–Oligodeoxynucleotide Analgoues, Ch. 6 in *Oligodeoxynucleotides[:] Antisense Inhibitors of Gene Expression*, J. S. Cohen (ed.), CRC Press, Inc., Boca Raton, FL, 1989, see pp. 119–136.

Zamecnik et al., "Inhibition of Rous Sarcoma Virus Replication and Cell Transformation by a Specific Oligodeoxynucleotide," *Proc. Nat. Acad. Sci. USA*, 75(1), 280–284 (1978).

Stephenson et al., "Inhibition of Rous Sarcoma Viral RNA Translation by a Specific Oligodeoxyribonucleotide," *Proc. Nat. Acad. Sci. USA*, 75(1), 285–288 (1978).

Myles et al., "Syntheses und Eigenschaften von Thymidylyl–(3'–>3')–, –(3'–>5')–und –(5'–>5')–thymidin," *Chem. Ber.*, 108, 2857–2871 (1975).

Rokos et al., "Über die Verseifung von Dinucleosidmonophosphorsäure–phenyl ester und die Isomerisierung der Internucleotid–Bindung," *Chem. Ber.*, 108, 2872–2877 (1975).

Agrawal et al., "Efficient Methods for Attaching Non–radioactive Labels to the 5' Ends of Synthetic Oligodeoxyribonucleotides," *Nucleic Acids Research*, 14(15), 6227–6245 (1986).

Van De Sande et al., "Parallel Stranded DNA," *Science*, 241, 551–557 (1988).

Zon, "Oligonucleotide Analogues as Potential Chemotherapeutic Agents," *Pharmaceutical Research*, 5(9), 539–549 (1988).

AUTORADIOGRAM OF THE SEQUENCING OF SV40TS17, SV40TAS17 AND SV40TAS17 (3'-3', 5'-5')

AUTORADIOGRAM OF THE CLEAVAGE OF $dT_{20}$ AND $dT_{20}$ (3'-3', 5'-5') WITH FRESH HUMAN SERUM;
FROM THE LEFT:
$dT_{20}$: REACTION AFTER 0, 5, 8, 11, 15 AND 30 MINUTES
$dT_{20}$ (3'-3', 5'-5'): REACTION AFTER 0, 5, 8, 11, 25, 30 AND 90 MINUTES

AUTORADIOGRAM OF THE SVpdE CLEAVAGE:
FROM THE LEFT: $dT_{20}$, $dT_{20}$ (3'-3', 5'-5') CLEAVAGE
OF $dT_{20}$(3'-3', 5'-5') AFTER 5, 15, 30, 45, 60, 90 MIN.,
MIX OF 0 MIN./15MIN, MIX OF 0 MIN/30MIN, CLEAVAGE
OF $dT_{20}$ AFTER 5, 15, 30, 45 MINUTES.

MODULATION OF THE EXPRESSION OF T-Ag BY ANTISENSE OLIGONUCLEOTIDES.
LINE 1: CELL LYSATE AFTER INHIBITION WITH 30 μM SV40TAS17 (3'-3', 5'-5')
LINE 2: CELL LYSATE WITHOUT INHIBITION.
M : SCALE

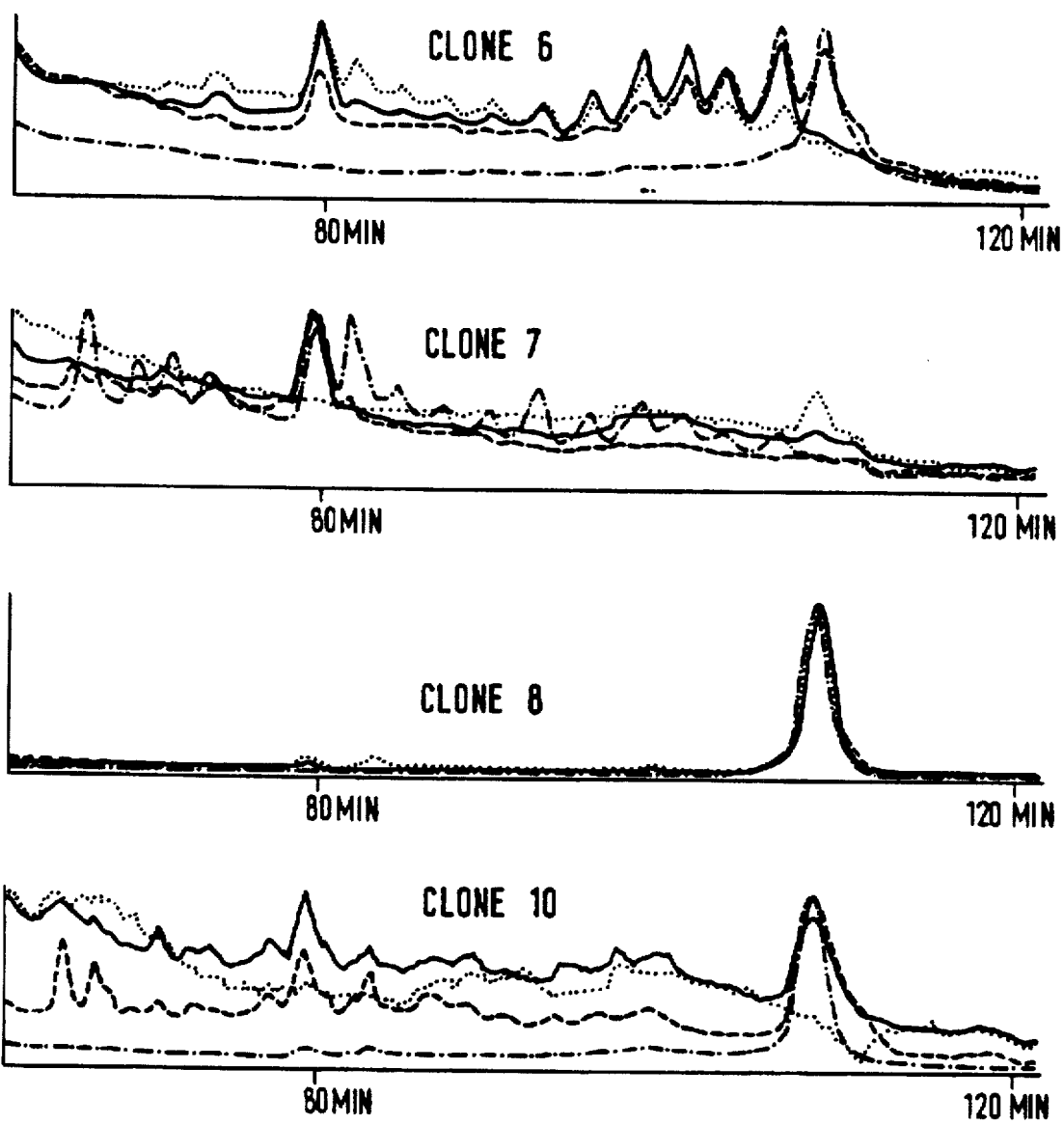

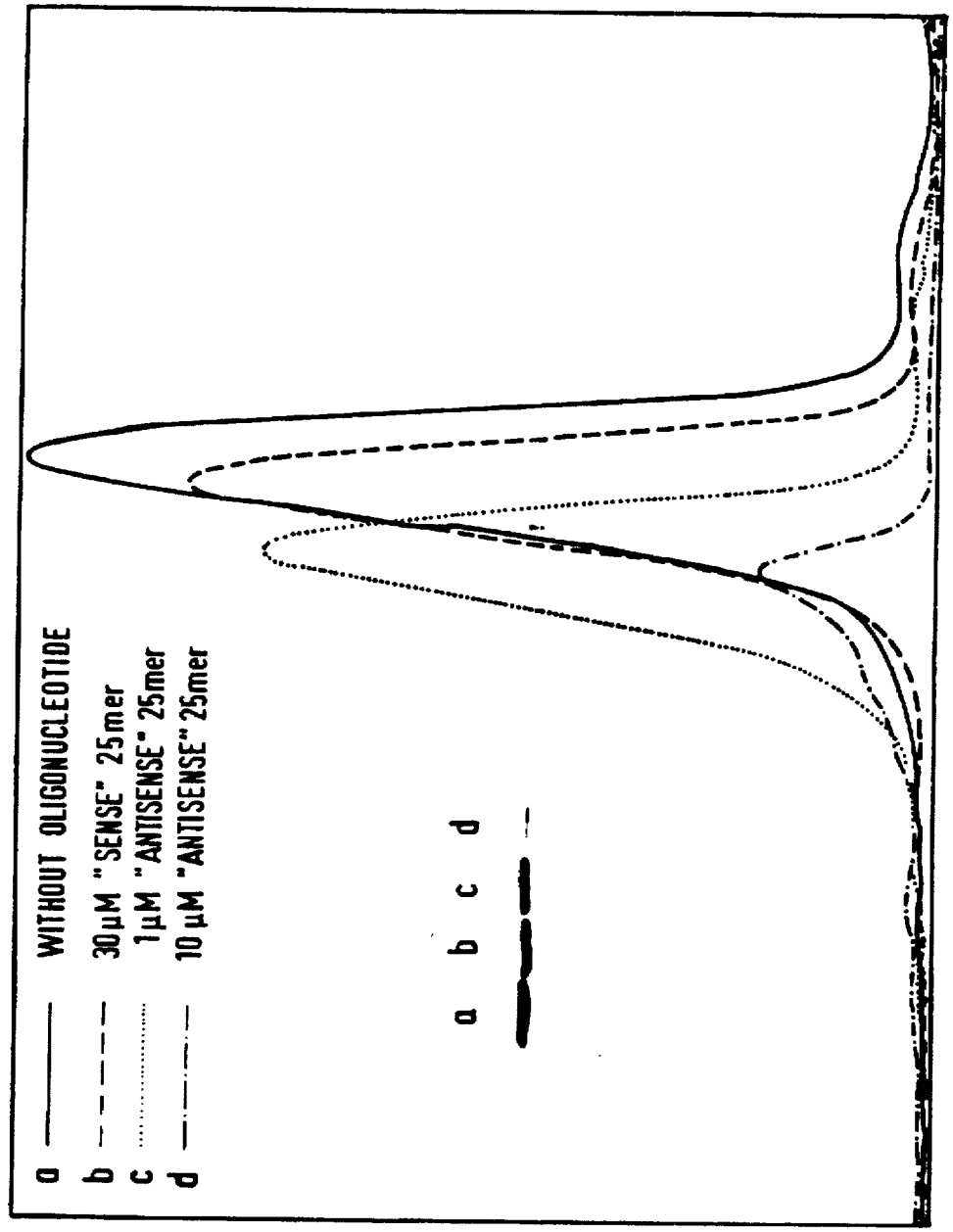

OLIGONUCLEOTIDE ANALOGS WITH TERMINAL 3'-3' OR 5'-5' INTERNUCLEOTIDE LINKAGES

This application is a continuation of application Ser. No. 07/723,440, filed Jun. 28, 1991, now abandoned.

Antisense oligonucleotides are defined as nucleic acid fragments whose sequence is complementary to the coding or sense sequence of a messenger RNA or to the codogenic strand of the DNA. Oligonucleotides of this type are increasingly being used to inhibit gene expression in vitro or in cell culture systems. There have been wide-ranging investigations of the use of such substances in medical therapy, for example as antiviral drugs. In biology, antisense RNA sequences have already been known for some time as naturally occurring regulators of gene expression in prokaryotes (T. Mizuno, M.-Y. Chou and M. Inouye, Proc. Natl. Acad. Sci. USA 81, 1966–1970 (1984)) and eukaryotes (S. M. Heywood, Nucleic Acids Res. 14, 6771–6772 (1986)) too. They bring about inhibition of translation by hybridizing with an appropriate messenger RNA. It has now been shown in numerous experiments that such antisense RNA sequences can also impede gene expression on insertion into bacteria (A. Hirashima, S. Sawaki, Y. Inokuchi and M. Inouye, PNAS USA 83, 7726–7730 (1986)) or eukaryotic cells (J. G. Izant and H. Weintraub, Cell 36, 1007–1015 (1984)), and display both antiviral (L.-J. Chang and C. M. Stoltzfus, J. Virology 61, 921–924 (1987)) and anti-oncogene (J. T. Holt, T. V. Gopal, A. D. Moutton and A. W. Nienhuis, PNAS USA 83, 4794–4798 (1986)) effects. The advantage of synthetic oligonucleotides compared with biological antisense RNA for such investigations is greater stability and easier obtainability. The latter relates to the synthetic techniques which have been greatly improved in recent times and make relatively short oligomers (of, for example, 12–30 bases) now relatively easy to obtain (E. Sonveaux, Bioorganic Chemistry 14, 274–325 (1986); Oligodeoxynucleotides, Antisense Inhibitors of Gene Expression, J. S. Cohen, ed., Macmillan Press, 1989; pages 7 et seq.). It has emerged that even such short oligomers are effective modulators of expression.

Moreover, such oligonucleotides may also act by binding to the DNA double strand with the formation of a triple helix. However, in order for both the antisense oligonucleotides and the triplex-forming oligonucleotides to be employed in biological systems it is necessary to meet the following requirements (Oligodeoxynucleotides, Antisense inhibitors of gene expression, J. S. Cohen ed. Macmillan Press, 1989, pages 1 et seq.):

1. they must, on the one hand, be readily soluble in water but, on the other hand, easily pass through the lipophilic cell membrane,
2. they must be sufficiently stable to degradation within the cell, that is to say be stable to nucleases,
3. they must form stable hybrids with intracellular nucleic acids at physiological temperatures,
4. the hybridization must be selective; the difference in the dissociation temperature from an oligonucleotide which yields mispairing must be sufficiently large for it still to be possible to wash out the latter specifically.

In 1978, Zamecznik and Stephenson (P. C. Zamecnik and M. Stephenson, PNAS USA 75, 280–284 and 285–288 (1978)) showed for the first time that unmodified oligonucleotides are able to inhibit the replication of Rous sarcoma viruses. However, the oligonucleotides were used in very high concentrations and, moreover, the experiments were mostly carried out in previously heated media in order to inactivate nucleases. The necessity for these measures is explained by the rapid enzymatic degradation to which foreign nucleic acids are subject in serum and in cells.

Thus, investigations were carried out at an early date with the aim of structurally modifying oligonucleotides so that they meet the abovementioned requirements better, in particular are better protected against intracellular degradation. These investigations were particularly concentrated on modification of the phosphodiester internucleotide linkage because this is, in the final analysis, the point of attack by all nucleases. Structurally modified internucleotide linkages can be divided in principle into a) nucleoside linkages with phosphorus as central atom. These in turn may be:
   ionic/chiral
   ionic/achiral
   neutral/chiral b) neutral/achiral phosphorus-free nucleoside linkages.

Thiophosphate and dithiophosphate linkages are among the structurally modified but still ionic internucleoside linkages. Thiophosphate-modified oligonucleotides (Oligodeoxynucleotides, Antisense inhibitors of gene expression, J. S. Cohen, ed. Macmillan Press, 1989, pages 97 et seq.) currently show the best inhibitory effects on gene expression in cell cultures, although this inhibition appears not to be bound to a specific sequence because inhibitory effects are shown even by those thiophosphate-modified oligonucleotides which are composed of only one nucleic acid unit, for example thiophosphate analogs of oligocytidylate. The use of thiophosphate-modified oligonucleotides continues to be limited by their chirality.

Since, however, the preparation of an oligonucleotide of n bases results in $2^n-1$ diastereomers, only a minute proportion of a product containing thiophosphate linkages has good hybridization properties.

The chirality problem is avoided in oligonucleotides with dithiophosphate internucleoside linkages (A. Grandas, William S. Marshall, John Nielsen and Martin H. Caruthers, Tetrahedron Lett. 20, 543–546 (1989), G. M. Porritt, C. B. Reese, Tetrahedron Lett. 30, 4713–4716 (1989)). However, to date, such compounds have been obtained only by complicated and multistage syntheses with high losses. This is why to date no wide-ranging investigations of the hybridization behavior, especially in cell cultures, have yet been carried out.

Another class of chemically modified oligonucleotides are those with non-ionic, that is to say neutral, internucleoside linkages. This type of modified structure includes oligonucleotides with phosphotriester or methylphosphonate internucleoside linkages (Oligodeoxynucleotides, Antisense inhibitors of gene expression, J. S. Cohen, ed. Macmillan Press, 1989, pages 79 et seq.).

It is common to both classes of compounds that the ionizable phosphate residue is replaced by an uncharged group. The introduction of a linkage of this type makes these oligonucleotide analogs resistant to nucleases, but they have the disadvantage of low solubility in aqueous medium.

Oligonucleotides with neutral/achiral internucleoside linkage have to date been obtainable only by replacing the phosphorus atom of the internucleoside linkage by another central atom. A siloxane linkage resembles the phosphoric ester linkage. Oligonucleotides with siloxane internucleoside linkages (K. K. Ogilvie, J. F. Cormier, Tetrahedron Lett. 26, 4159 (1985), H. Seliger, G. Feger, Nucl. Nucl. 6 (182), 483–484 (1987)) have been synthesized and are stable to nucleases.

Oligonucleotides with carbonate, acetal or carboxamide internucleoside linkages are disclosed in M. Matteucci, Tetrahedron Lett. 31, 2385–2388 (1990), J. R. Tittensor, J. Chem. Soc. C, 1971, page 2656 and J. Coull et al., Tetrahedron Lett. 28, page 745. Nuclease-resistant oligonucleotide analogs have also been generated without modifying the phosphodiester internucleotide linkage, by employing sugar residues with an altered configuration. This took place by synthesizing oligonucleotide analogs in which the nucleobases are attached α-glycosidically (Oligodeoxynucleotides, Antisense inhibitors of gene expression, J. S. Cohen, ed. Macmillan Press, 1989, pages 119 et seq.). However, oligonucleotide analogs of this type are difficult to obtain preparatively because they must be synthesized starting from sugar and base. Moreover, in some cases they show abnormal behavior with regard to the direction of hybridization.

The invention relates to oligonucleotides of the formulae I or II

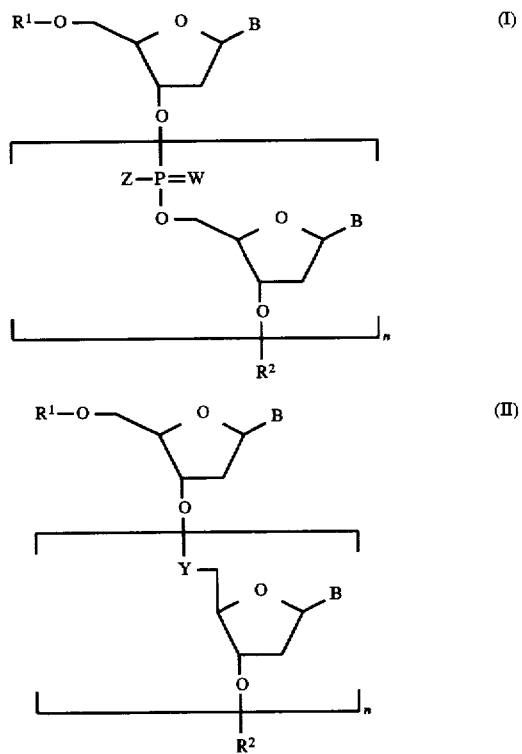

in which $R^1$ is hydrogen or a radical of the formula III

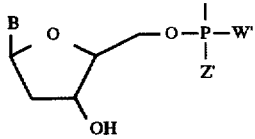

$R^2$ is hydrogen or a radical of the formula IV

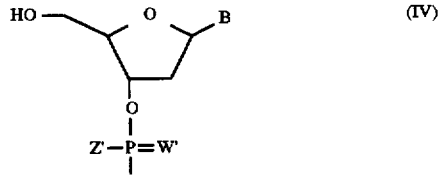

but where at least one of the radicals $R^1$ or $R^2$ is a radical of the formula III or IV;

B is a base such as, for example, natural bases such as adenine, thymine, cytosine, guanine or unnatural bases such as, for example, purine, 2,6-diaminopurine, 7-deazaadenine, 7-deazaguanine or $N^4,N^4$-ethenocytosine or their prodrug forms;

W and W' are, independently of one another, oxygen or sulfur;

Z and Z' are, independently of one another, $O^-$; $S^-$; $C_1$–$C_{18}$-alkoxy, preferably $C_1$–$C_8$-alkoxy, particularly preferably $C_1$–$C_3$-alkoxy, especially methoxy; $C_1$–$C_{18}$-alkyl, preferably $C_1$–$C_8$-alkyl, particularly preferably $C_1$–$C_3$-alkyl, especially methyl; $NHR^3$ with $R^3$=preferably $C_1$–$C_{18}$-alkyl, particularly preferably $C_1$–$C_8$-alkyl, especially $C_1$–$C_4$-alkyl, or $C_1$–$C_4$-alkoxy-$C_1$–$C_6$-alkyl, preferably methoxyethyl; $NR^3R^4$ in which $R^3$ is as defined above and $R^4$ is preferably $C_1$–$C_{18}$-alkyl, particularly preferably $C_1$–$C_8$-alkyl, especially $C_1$–$C_4$-alkyl, or in which $R^3$ and $R^4$ form, together with the nitrogen atom carrying them, a 5–6-membered heterocyclic ring which can additionally contain another hetero atom from the series comprising O, S, N, such as, for example, morpholine;

Y is a radical from the series comprising O—Si(R)$_2$, OCH$_2$, C(O)NR or O—CH$_2$—C(O) in which R is $C_1$–$C_6$-alkyl, aryl or C5- or $C_6$-cycloalkyl; and n is an integer from 5 to 60, preferably 10–40 and particularly preferably 15–25, and the physiologically tolerated salts thereof.

In this connection, aryl means, for example, phenyl, phenyl substituted (1–3 times) by $C_1$–$C_6$-alkyl, $C_1$–$C_6$-alkoxy and/or halogen.

Oligonucleotides of the formula I are preferred.

Furthermore preferred are oligonucleotides of the formula I in which $R^2$ is a radical of the formula IV and $R^1$ is hydrogen; $R^1$ and $R^2$ are a radical of the formulae III and IV respectively; or $R^2$ is hydrogen and $R^1$ is a radical of the formula III where either W or Z in the latter case is not oxygen.

Furthermore, particular mention may be made of oligonucleotides of the formula I in which W is oxygen or both Z and W are oxygen.

Very particularly preferred oligonucleotides of the formula I are those in which $R^2$ is a radical of the formula IV and $R^1$ is hydrogen.

Furthermore, mention may be made of oligonucleotides of the formulae I and II which are additionally substituted by groups which favor intracellular uptake, which act in vitro or in vivo as reporter groups, and/or groups which on hybridization of the oligonucleotide with biological DNA or RNA attack this DNA or RNA molecule, with bond formation or cleavage.

Examples of groups which favor intracellular uptake are lipophilic radicals such as alkyl radicals, for example with up to 18 carbon atoms or cholesteryl or conjugates which utilize natural carrier systems, such as, for example, bile acid or peptides for the appropriate receptor (for example receptor-mediated endocytosis). Examples of reporter groups are fluorescent groups (for example acridinyl, dansyl, fluoresceinyl) or chemiluminescent groups such as, for example, acridinium ester groups.

Oligonucleotide conjugates which bind to and/or cleave nucleic acids contain acridine (N. Thuong et al., Tetrahedron Left. 29, page 5905, 1988), psoralen (U. Pieles et al., Nucleic Acid Res. Vol. 17, page 285, 1989) or chloroethylaminoaryl conjugates (Oligodeoxynucleotides, Antisense inhibitors of gene expression, J. S. Cohen, ed. Macmillan Press, 1989, pages 173 et seq.).

BRIEF DESCRIPTION OF THE DRAWINGS

FIG. 5 shows stability of Xelev 1 (clone 6 and clone 7) and Xelev 2 (clone 8 and clone 10) in serum.

FIG. 6 shows inhibition of the biosynthesis of oncoprotein p53 by an antisense oligonucleotide.

Figure 1:
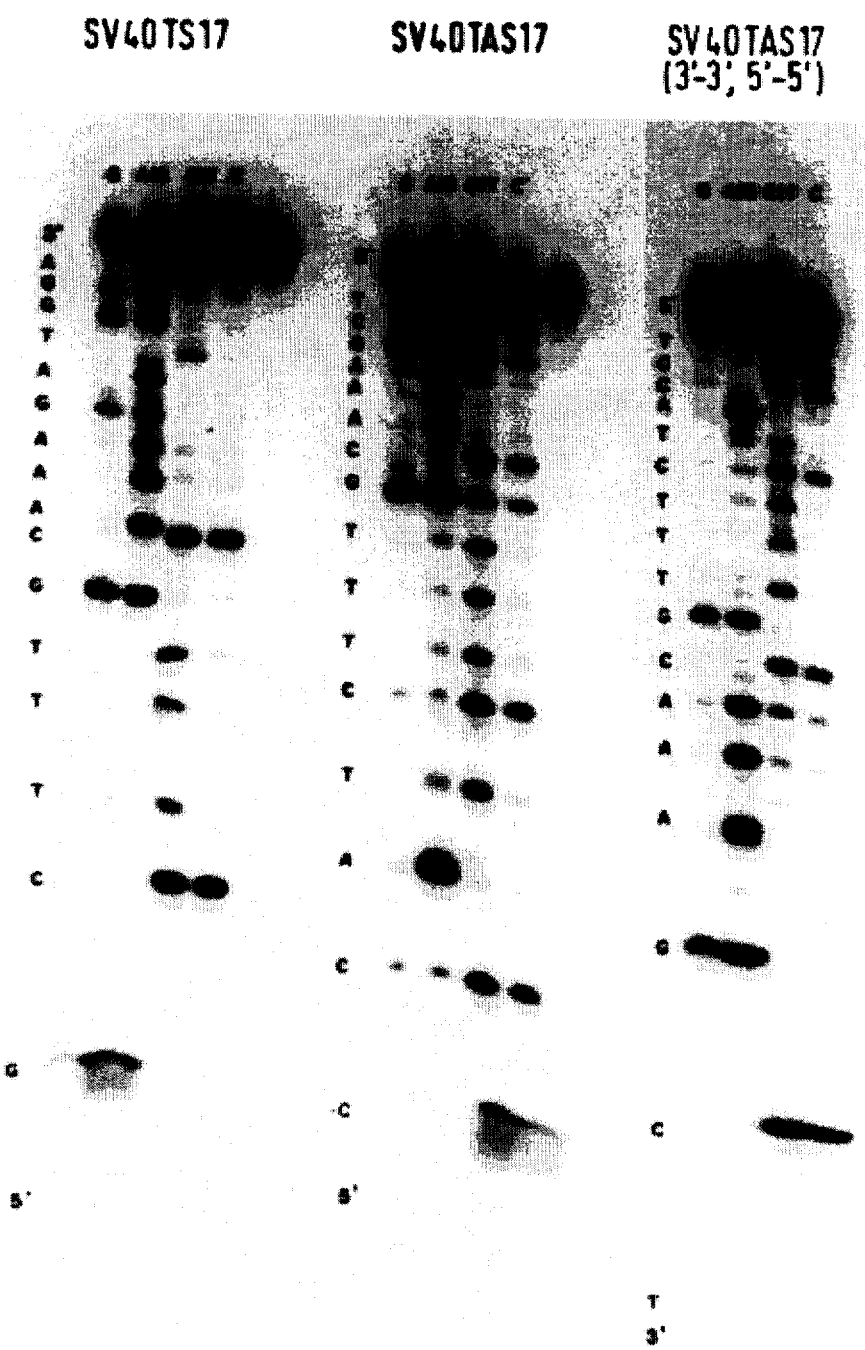
FIG. 1 shows an autoradiogram of the sequencing of oligonucleotides SV40TS17, SV40TAS17 and SV40TAS17 (3'—3', 5'—5').

The characteristic structural modification of these oligonucleotides is that the internucleotide linkages at both chain ends are altered, that is to say are 3'—3' or 5'—5' linkages in place of biological 3'-5' linkages. We have found, surprisingly, that this minimal structural modification suffices to stabilize such compounds against nuclease degradation.

As is described hereinafter, the only slight structural modification results in a hybridization behavior which is almost identical to that of the biological oligonucleotides. This also results in these compounds being generally utilizable as inhibitors of gene expression in cell cultures.

To date there is no indication in the literature of the preparation of oligonucleotide analogs with 3'—3' and 5'—5' internucleoside linkages at both chain ends and the use thereof as antisense oligonucleotides. Analogs of dinucleoside phosphates which contain either 3'—3' or 5'—5' linkages have for many years been obtained as main products (A. Myles, W. Hutzenlaub, G. Reitz and W. Pfleiderer, Chem. Ber. 108, 2857–2871 (1975); H. Rokos, A. Myles, W. Hutzenlaub and W. Pfleiderer, Chem. Ber. 108, 2872–2877 (1975); J. Tomasz, Nucl. Nucl. 2. (1), 51–61 (1983); M. Nemer, N. Theriault, A. Schifman and K. K. Ogilvie, VIth International Round Table, Nucleosides, Nucleotides and their biological Applications, La Grande Motte, ed. J. L. Imbach, 94–96 (1984)) or byproducts (R. Letsinger, K. K. Ogilvie, J. Amer. Chem. Soc. 89, 4801–4802 (1967)) of appropriate condensation and have been investigated. However, dimers of this type have too low a melting point to be capable in principle of stable hybridization with cellular nucleic acids. Oligonucleotides which have a 5'—5' linkage at only one end have been synthesized to introduce an attachment point for reporter groups in gene probes (S. Agrawal, C. Christodoulou, M. J. Gait, Nucleic Acids Res 14, 6227–6245 (1986)). However, their hybridization behavior has not to date been investigated. Self-complementary oligonucleotides which have in the middle of the molecule a single 3'—3' or 5'—5' linkage have been prepared for biophysical investigations (J. H. van de Sande, N. B. Ramsing, M. W. Germann, W. Elhorst, B. W. Kalisch, E. V. Kitzing, R. T. Pon, R. C. Clegg, T. M. Jovin, Science 241, 551–557 (1988)).

The preparation of oligonucleotides with inverted terminal 3'—3' and 5'—5' linkage is carried out in the same way as the synthesis of biological oligonucleotides in solution or, preferably, on a solid phase, where appropriate with the assistance of an automatic synthesizer.

The invention therefore also relates to a process for preparing the oligonucleotides of the formula I, which comprises a) reacting a nucleotide unit with 3'- or 5'-terminal phosphorus(III) or phosphorus(V) groups or the activated derivative thereof with another nucleotide unit with free 3'- or 5'-terminal hydroxyl group or b) synthesizing the oligonucleotide by fragments in the same way, where appropriate eliminating one or more protective groups temporarily introduced into the oligonucleotides obtained as in (a) or (b) to protect other functions, and, where appropriate, converting the oligonucleotides of the formula I obtained in this way into their physiologically tolerated salt.

The starting component employed for the solid-phase synthesis is a support resin to which the first nucleoside monomer is attached via the 5'-OH group. Used to prepare this component is a support resin prepared by methods known from the literature (T. Atkinson, M Smith in Oligonucleotide Synthesis, M. J. Gait (ed), 35–49 (1984)), preferably silica gel or controlled pore glass, which is functionalized with amino groups. It is reacted with a nucleoside derivative which is protected on the nucleobase and on the 3'-OH group and which has previously been converted into the 5'-(p-nitrophenyl succinate). The protective groups preferably employed for the bases are acyl groups, for example benzoyl, isobutyryl or phenoxyacetyl. The 3' position is preferably protected by dimethoxytrityl protective group which can be introduced as described in M. D. Matteucci, M.-H. Caruthers, Tetrahedron Letters 21 (1980) pages 3243–3246. Further synthesis of the oligonucleotide chain up to the penultimate chain member is carried out by methods known from the literature, preferably using nucleoside 3'-phosphoramidites or nucleoside 3'-H-phosphonates protected on the 5'-OH group by dimethoxytrityl groups. Employed as the last chain member is once again a nucleoside 5'-phosphoramidite or nucleoside H-phosphonate protected on the 3'-OH group, preferably with dimethoxytrityl. The preparation of an oligonucleotide chain of this type with inverted terminal internucleotide linkages is shown diagrammatically hereinafter. (Phosphoramidite cycle to prepare oligonucleotides with 3'—3' and 5'—5' linkages at the ends). The preparation of oligonucleotides with 3'—3' or 5'—5' linkages is carried out correspondingly.

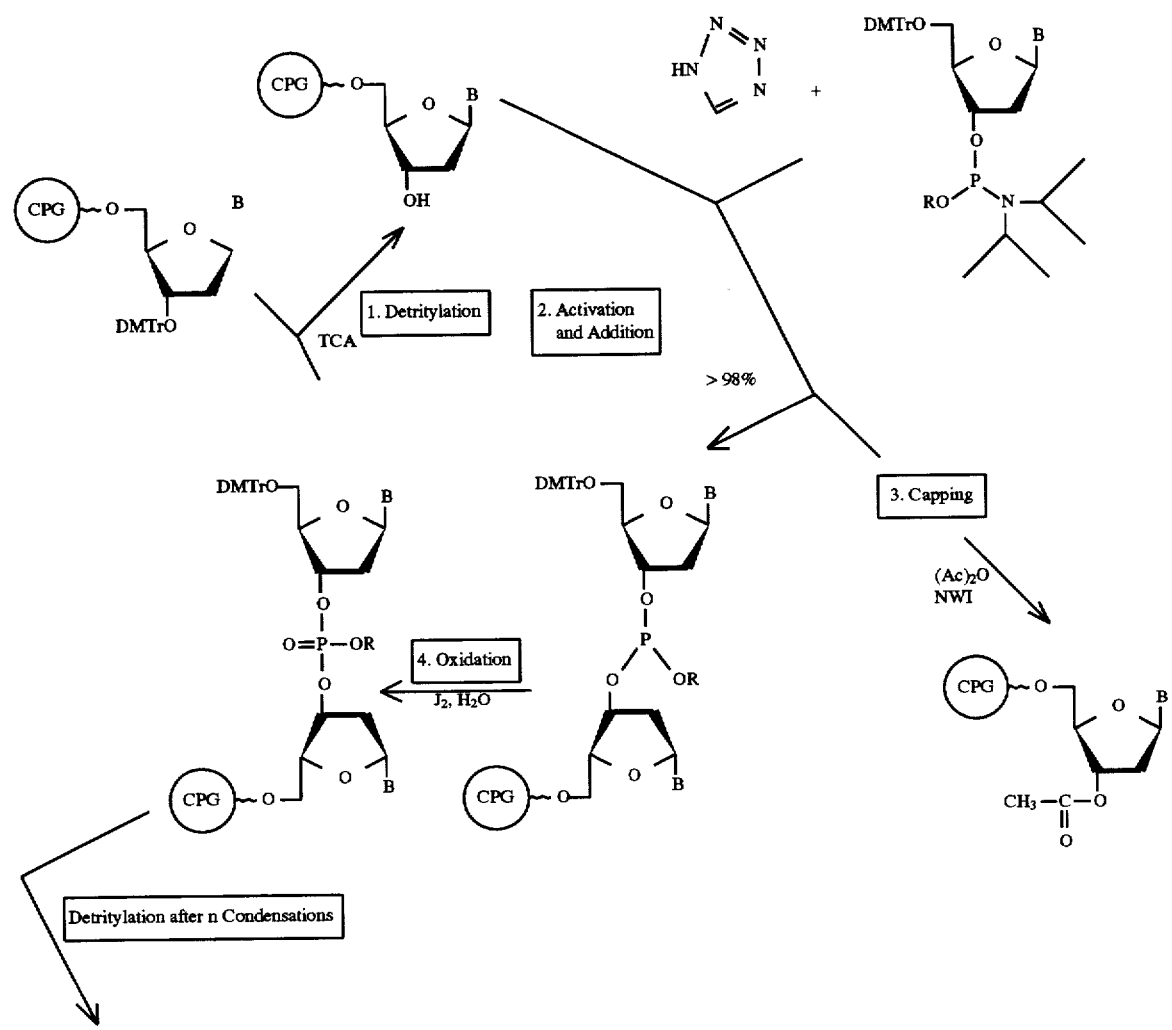

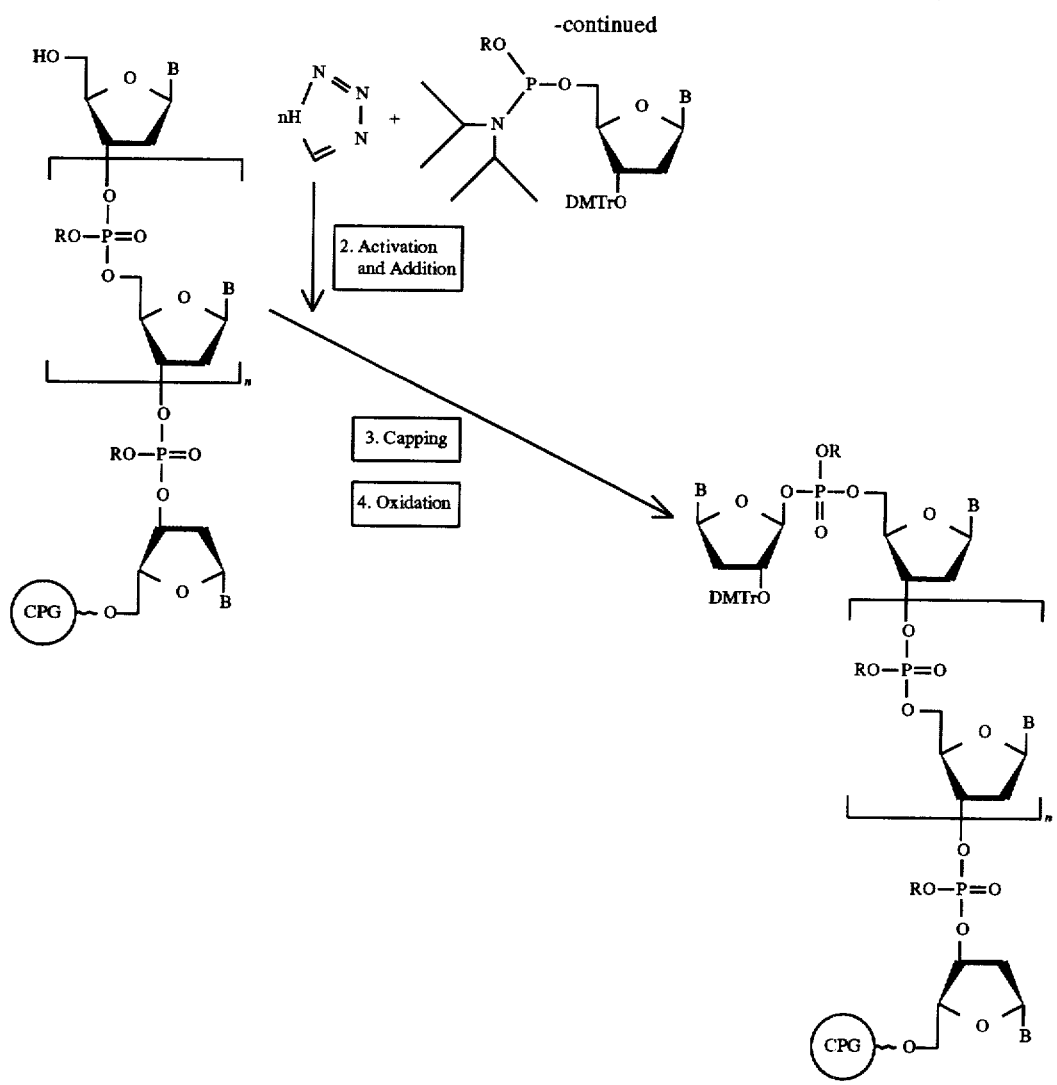

Structure and sequence analysis is carried out by initial terminal labeling of the synthesized oligonucleotide with 3'—3' and 5'—5' ends. This is effected by radiolabeling, preferably using 5'-γ-$^{32}$P-ATP/polynucleotide kinase. This radiolabeling takes place on the free 5'-OH group, that is to say at the opposite end of the nucleotide chain compared with an oligonucleotide with only biological 3'-5' linkages. Subsequent sequence analysis is then carried out by methods known from the literature, preferably by base-specific random cleavage as described by Maxam and Gilbert (A. M. Maxam and W. Gilbert, Methods in Enzymology 65, 499–560 (1980)). Because the radiolabeling is at the "opposite" end of the molecule, the reading of the sequence also now takes place in the opposite direction compared with an oligonucleotide with biological 3'-5' linkage. A detailed description of the test is given in Example 6.

The oligonucleotides of the formulae I and II are used for chemical hybridization methods, which are based on the attachment to double- or single-stranded nucleic acids, for regulation or suppression of the biological functions of nucleic acids, and for selective suppression of the expression of viral genome functions and for prophylaxis and therapy of viral diseases, for suppressing oncogene function and for therapy of cancers.

The behavior of an oligonucleotide of the formula I or II synthesized according to the invention and dissolved in blood serum can be regarded as a measure of the stability in vivo. The general test is described in Example 7; a corresponding in vitro test with a solution of snake venom phosphodiesterase is described in Example 8. The oligonucleotides according to the invention are degraded much more slowly than the 3'-5' oligonucleotides.

Example 11 demonstrates the serum stability of oligonucleotides with terminal inverted 3'—3' linkage.

The hybridization behavior is evident from model experiments as described in Example 9, in which a number of SV40-specific sequences which have been prepared according to the invention with, in each case, a 3'—3' and 5'—5' end show on hybridization with the appropriate opposite strand of SV40 DNA a melting point which is only negligibly lower than the melting point measured on hybridization with a corresponding sequence not synthesized according to the invention, that is to say without 3'—3' and 5'—5' end.

The activity of the oligonucleotides provided according to the invention with terminal 3'—3' and 5'—5' linkages as inhibitors of gene expression is evident from the suppression of the growth of the virus SV40.

EXAMPLE 1

Synthesis of 3'-O-DMTr-deoxyribonucleoside 5'-(N, N-diisopropyl-β-cyanoethyl)phosphoramidite 4

The reaction scheme starting from the base-protected nucleosides is depicted below:

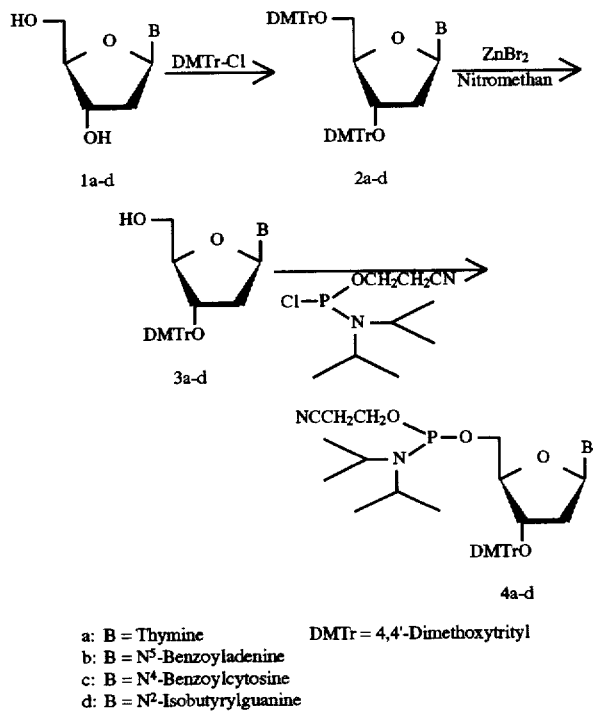

a: B = Thymine  DMTr = 4,4'-Dimethoxytrityl
b: B = $N^5$-Benzoyladenine
c: B = $N^4$-Benzoylcytosine
d: B = $N^2$-Isobutyrylguanine A) Preparation of the 3',5'-O-bis-DMTr-deoxyribonucleosides 2

| Mixture: | 6 mmol of dT, dA$^{bz}$, dC$^{bz}$ or dG$^{ibu}$ |
|---|---|
| | 14.4 mmol of DMTr-Cl |
| | 14.0 mmol of TEA abs. |

The deoxyribonucleoside 1 is dissolved in 50 ml of absolute pyridine and, at 0° C., triethylamine and dimethoxytrityl chloride are added. The mixture is then left to stir at room temperature for 24 h, following the reaction by thin-layer chromatography (mobile phase: CH$_2$Cl$_2$/MeOH 9:1). The reaction is stopped by addition of methanol, the solvent is stripped off, and the residue is taken up in dichloromethane. The organic phase is washed several times with 1M NH$_4$HCO$_3$ solution and with H$_2$O, dried over Na$_2$SO$_4$ and concentrated in a rotary evaporator. The 3',5'-ditritylated product 2 can be purified from excess tritanol and from 5'-DMTr-dN by column chromatography (column material: silica gel 60 H, eluent: CH$_2$Cl$_2$ with increasing methanol content, where the ditritylated deoxynucleosides are eluted at 1–1.5% MeOH).

Yield: 73–85% of theory.

B) Specific Elimination of the 5'-dimethoxytrityl Group

Reference: M. D. Matteucci and M. H. Caruthers, Tetrahedron Lett. 21, 3243–3246 (1980)

| Mixture: | 3 mmol of 3',5'-O-bis-DMTr-dN 2 |
|---|---|
| | 15 mmol of ZnBr$_2$ |
| | 200 mmol of absolute nitromethane |

The solution of 3',5'-O-bis-DMTr-dN 2 in 100 ml of nitromethane is added at 0° C. to the suspension of zinc bromide in a further 100 ml of nitromethane. In the case of the protected deoxyadenosine, the reaction was continued while cooling in order to avoid depurination. Nevertheless, the elimination is complete after only 60 min with this nucleoside, as can be established by thin-layer chromatography. In the case of thymidine and deoxyguanosine the reaction is likewise complete after 60 min at room temperature, whereas the 5'-detritylation of bis-DMTr-deoxycytidine takes place only incompletely. In this instance the reaction was stopped after 3 hours in order to avoid elimination of the 3'-dimethoxytrityl group too. The reaction is stopped by adding 200 ml of 1M NH$_4$Ac solution; the product 3 is extracted with 200 ml of CH$_2$Cl$_2$, the organic phase is washed again with saturated NaCl solution and with H$_2$O and dried over Na$_2$SO$_4$, and the solvent is removed by distillation in vacuo.

Most of the tritanol can be removed by precipitating the crude product in about 500 ml of n-hexane at −15° C. Purification is then carried out by chromatography on a silica gel 60 H column with dichloromethane with increasing methanol content as eluent. The R$_f$ values of the 3'-DMTr-deoxyribonucleosides differ from the corresponding 5'-tritylated monomers in the following way (mobile phase: CH$_2$Cl$_2$/MeOH 24:1):

| | 3'-DMTr-dN | 5'-DMTr-dN |
|---|---|---|
| dT | 0.28 | 0.21 |
| dA$^{bz}$ | 0.55 | 0.29 |
| dC$^{bz}$ | 0.53 | 0.31 |
| dG$^{ibu}$ | 0.32 | 0.14 |

Yields: 48–65% of theory.

C) Preparation of 3'-O-DMTr-deoxyribonucleoside 5'-(N,N-diisopropyl-β-cyanoethyl)phosphoramidite 4

| Reference: | H. Köster, Nucleic Acids Res. 12, 4539–4557 (1984) |
|---|---|
| Mixture: | 1 mmol of 3'-O-DMTr-deoxyribonucleoside 3 |
| | 1.5 mmol of chloro-N,N-diisopropylamino-β-cyanoethoxyphosphine |
| | 4 mmol of diisopropylamine |

The phosphitylation reactions were carried out in analogy to the method described by Köster et al. (28) to prepare the 5'-O-DMTr-deoxyribonucleoside 3'-phosphoramidites. Under argon, diisopropylamine followed by the phosphorylation reagent was added to the solution of the protected nucleosides in absolute CH$_2$Cl$_2$. After 30 min the reaction was stopped by adding 30 ml of ethyl acetate, the solution was extracted 3× with saturated NaCl solution, the organic phase was dried over Na$_2$SO$_4$, and the solvent was removed by distillation in vacuo. The crude product was purified by column chromatography (column material: silica gel 60 H, eluent: petroleum ether/dichloromethane/triethylamine 45:45:10).

Yield of 4a: 93% of theory.

EXAMPLE 2

Preparation of Thymidylyl-Thymidine with a 3'—3' Phosphodiester Linkage

The reaction route for preparing the dimer block is indicated below.

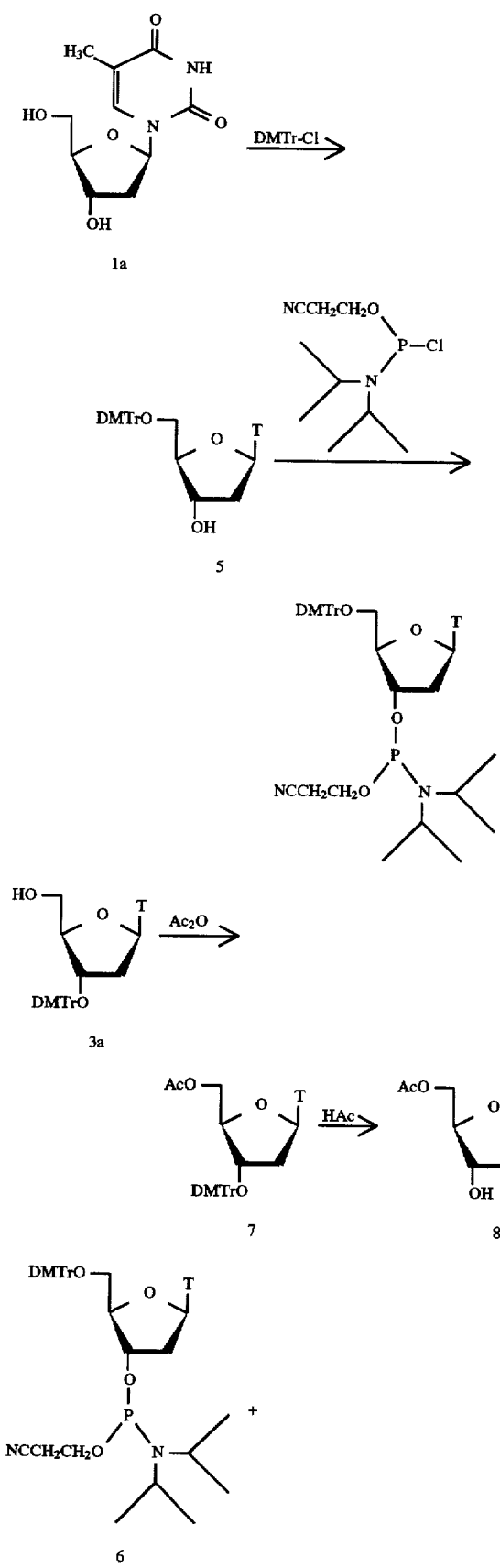

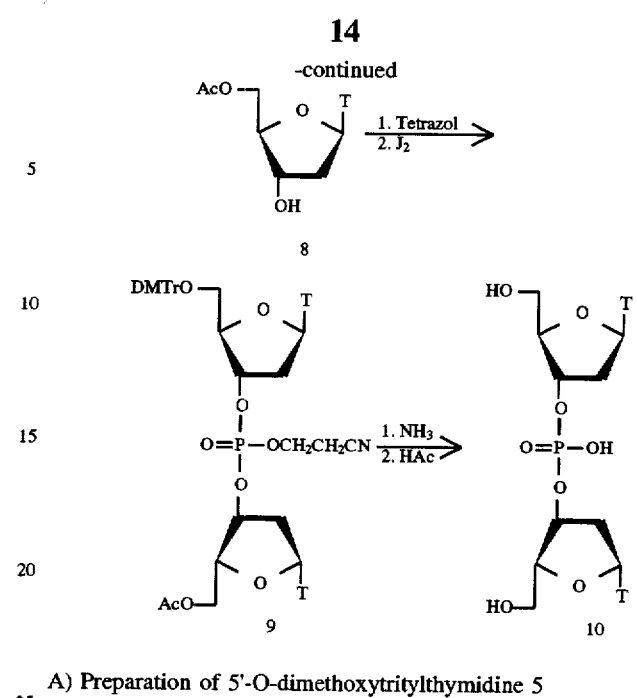

A) Preparation of 5'-O-dimethoxytritylthymidine 5

| Mixture: | 20 mmol of thymidine (4.84 g) 24 mmol of 4,4'-dimethoxytrityl chloride (8.2 g) 1 mmol of dimethylaminopyridine (122 mg) 28 mmol of abs. triethylamine (3.8 ml) |
|---|---|

The preparation of 5 was carried out by the method of R. A. Jones (G. S. Ti, B. L. Gaffney and R. A. Jones, J. Amer. Chem. Soc. 104, 1316–1319 (1982)). Thymidine was dried by coevaporation 3 times with 50 ml of absolute pyridine each time and taken up in 100 ml of pyridine and, while cooling in ice, 4,4'-DMTr-Cl and DMAP as catalyst were added. The reaction was monitored by thin-layer chromatography (mobile phase $CH_2Cl_2$/MeOH 9:1); it was possible to stop the reaction by adding 100 ml of water after 4 hours. The solution was extracted 3× with ether, the organic phase was dried and concentrated in a rotary evaporator, and the residue was purified by recrystallization in benzene.

Yield: 9.68 g of DMTr-dT (89%)

B) Preparation of 5'-O-dimethoxytritylthymidine 3'-O-(N, N-diisopropyl-β-cyanoethyl)phosphoramidite 6

The preparation and purification of 6 were carried out as described for the synthesis of the 3'-O-DMTr 5'-phosphoramidites 4 (Example 1, C).

C) Preparation of 5'-O-acetylthymidine 8

| Mixture: | 2.0 mmol of 3'-O-DMTr-dT 3a (1.1 g) 0.1 mmol of dimethylaminopyridine (12.2 mg) 4 ml of acetic anhydride |
|---|---|

Reference: A. M. Michelson and A. R. Todd, J. Org. Chem. 1955 2632–2638 (modified)

$Ac_2O$ was added dropwise to the solution of 3'-O-DMTr-dT and DMAP in 20 ml of absolute pyridine cooled in ice. After a reaction time of 3 hours, conversion was complete (TLC check; mobile phase: $CH_2Cl_2$/MeOH 24:1). The product 7 was precipitated in 400 ml of ice-water, and the white precipitate was filtered off with suction, washed with ice-water and dried.

Yield: 1.02 g of 3'-O-DMTr-5'-O-Ac-dT (88%)

To eliminate the 4,4'-dimethoxytrityl group, 7 was stirred in 10 ml of 80% strength acetic acid at room temperature.

After 3 hours the reaction was stopped by adding 100 ml of ice-water; this resulted in 4,4'-dimethoxytritanol separating out as a white precipitate. It was filtered off with suction and the aqueous filtrate was concentrated in a rotary evaporator. The oily residue was taken up in a little $CH_2Cl_2$ and precipitated in 200 ml of n-hexane at $-15°$ C.

Yield: 455 mg of 5'-O-acetylthymidine (94%)

D) Preparation of thymidylyl-(3'—3')thymidine 10

| Mixture: | 1.0 mmol of 5'-O-DMTr-thymidine 3'-O-(N,N-diisopropyl-β-cyanoethyl)phosphoramidite 6 (705.8 mg) |
|---|---|
| | 0.9 mmol of 5'-O-acetylthymidine 8 (253 mg) |
| | 2.6 mmol of tetrazole (182 mg) |
| | 9.0 mmol of $I_2$ (1.14 g) |

It was possible to synthesize the dimer block 10 by the method described by Köster (H. Köster, Nucleic Acids Res. 12, 4539–4557 (1984)) for the preparation of 3'–5'-nucleoside dimers. The mixture of 5'-O-acetylthymidine and tetrazole was dissolved in 30 ml of absolute $CH_3CN$ and, under argon, added to the phosphoramidite. The mixture was stirred overnight, then a solution of 9 mmol of $I_2$ in 30 ml of acetonitrile/pyridine/water (24:5:1) was added and, after a further 15 minutes, the excess iodine was reduced by 5 ml of a 40% strength $H_2SO_3$ solution. The solution was then concentrated, the residue was taken up in $CH_2Cl_2$ and washed 2× with saturated $NaHCO_3$ solution, and the solvent was then removed by distillation. It was possible to purify the crude product by column chromatography (column material: silica gel 60 H; eluent: ethyl acetate/dichloromethane 50:50).

Yield: 665 mg (75%)

To eliminate the acetyl and β-cyanoethyl group, the dimer was treated with 5 ml of concentrated $NH_3$ at room temperature for 1 hour; it was possible to remove the 4,4'-dimethoxytrityl group with 80% strength acetic acid.

EXAMPLE 3

Preparation of Thymidylyl-Thymidine with 5'—5'-Phosphodiester Linkage 14

The following scheme shows the preparation of 14.

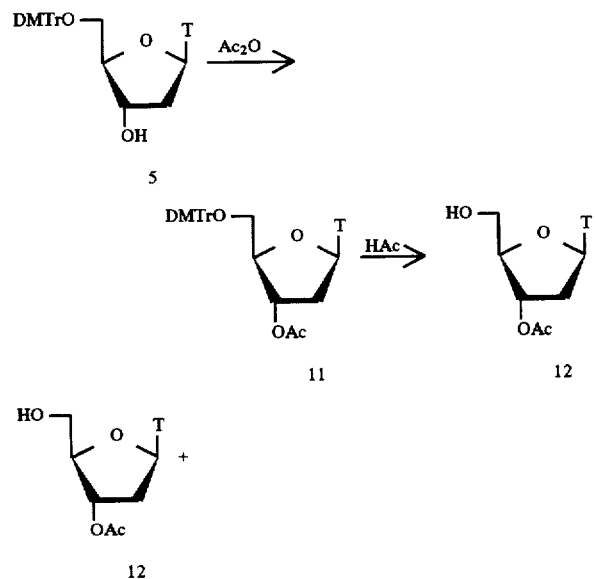

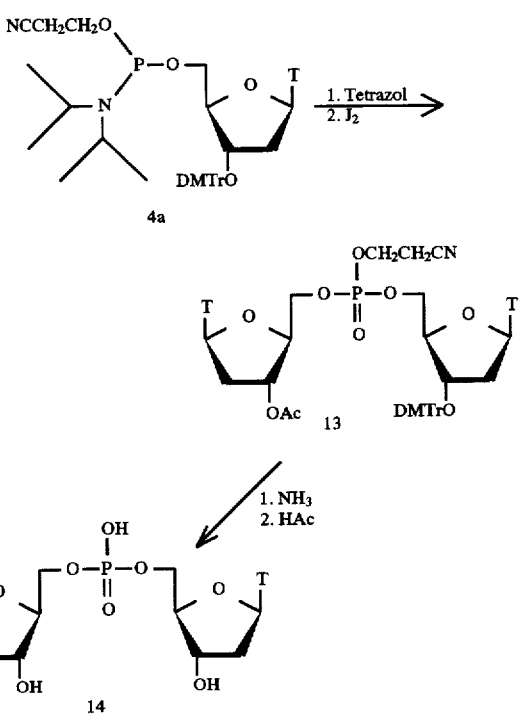

The individual reaction steps for synthesizing the intermediates were carried out by the methods described in Example 2. It was possible to verify the structure of the two dimer blocks by FAB mass spectrometry and $^1H$ nuclear magnetic resonance spectroscopy.

EXAMPLE 4

Loading of CPG 10-1400 Support Material with 3'-O-dimethoxytrityldeoxyribonucleoside 5'-O-succinate The CPG support was functionalized with 3-aminopropyl chains by the method of Atkinson and Smith (T. Atkinson, M. Smith in Oligonucleotide Synthesis, M. J. Gait (ed), 35–49 (1984)).

A) Preparation of 3'-O-DMTr-deoxyribonucleoside 5'-O-succinate 15

| Mixture: | 1.0 mmol of 3'-O-DMTr-dN 3 |
|---|---|
| | 0.8 mmol of succinic anhydride (80 mg) |
| | 0.5 mmol of dimethylaminopyridine (61 mg) |

The reaction of succinic anhydride with the 5'-OH group of the deoxyribonucleosides was carried out in each case in 5 ml of absolute pyridine with DMAP as catalyst at room temperature overnight. After the conversion was complete, the solution was concentrated and the pyridine was removed by azeotropic distillation with toluene 3 times. The residue was taken up in dichloromethane, and the organic phase was washed with 10% strength ice-cold citric acid solution and $H_2O$ and concentrated in vacuo. The crude product was dissolved in about 3 ml of toluene and precipitated in 200 ml of n-hexane.

Yields: 79–84%

B) Preparation of the 3'-O-DMTr-deoxyribonucleoside 5'-(p-nitrophenyl succinate) 16 and Support Loading (See Scheme Below)

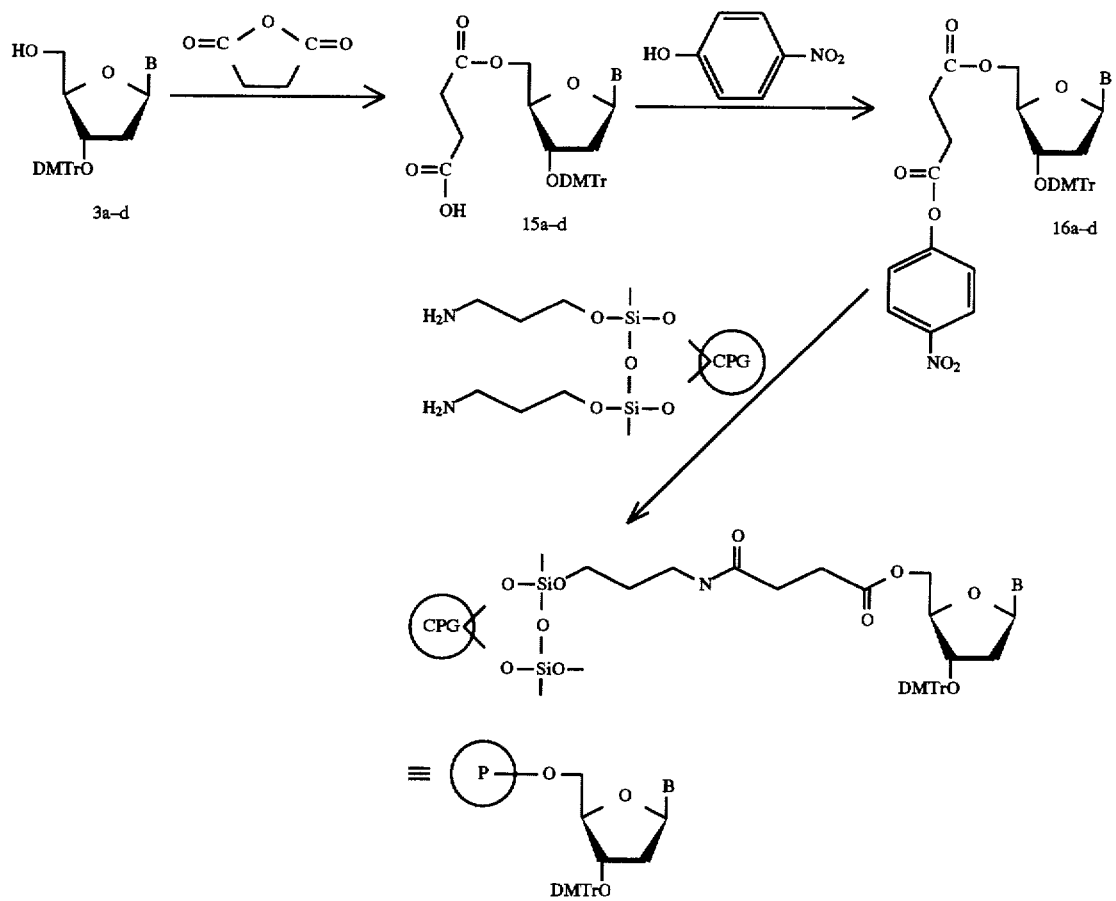

Mixture: 0.8 mmol of 3'-O-DMTr-dN 5'-O-succinate 15
0.8 mmol of p-nitrophenol (112mg)
2.0 mmol of dicyclohexylcarbodiimide (412 mg)
3 g of functionalized CPG 10-1400

The protected succinylated deoxyribonucleoside was added to a solution of p-nitrophenol in 5 ml of absolute dioxane and 0.2 ml of pyridine, and subsequently DCCI was added as condensing agent. After only a short time dicyclohexylurea precipitated out, and TLC ($CH_2Cl_2$/MeOH 9:1) after 3 hours showed complete conversion. The precipitate was filtered off with suction under argon and the filtrate was immediately added to a suspension of the functionalized support material in 15 ml of absolute DMF. 0.8 ml of triethylamine was added and the mixture was shaken overnight. The loaded support was then filtered off with suction, washed with methanol and ether and dried on a desiccator. The loading of the support was determined by spectrometry. A sample of the support (about 2 mg) is treated with 10 ml of a 0.1N solution of p-toluenesulfonic acid in acetonitrile to eliminate the 4,4'-dimethoxytrityl cation, and the loading of the support can be calculated in μmol/g by measurement of the absorption of the solution at 498 nm and using the equation

| $\dfrac{OD_{498}/ml \times 10\ ml \times 14.3\ (\text{const.})}{\text{mg of support}}$ | |
|---|---|
| Results: | 3'-DMTr-dT - support: | 23 μmol/g |
| | 3'-DMTr-dG$^{ibu}$ - support: | 21 μmol/g |

-continued

| $\dfrac{OD_{498}/ml \times 10\ ml \times 14.3\ (\text{const.})}{\text{mg of support}}$ | |
|---|---|
| 3'-DMTr-dA$^{bz}$ - support: | 21 μmol/g |
| 3'-DMTr-dC$^{bz}$ - support: | 15 μmol/g |

To block unreacted amino groups, the loaded support was shaken with a solution of 1 ml of acetic anhydride and 50 mg of dimethylaminopyridine in 15 ml of absolute pyridine at room temperature for 1 hour, then filtered off with suction, washed with methanol and ether and dried.

EXAMPLE 5 a) Synthesis of Oligonucleotides with Terminal 3'—3' and 5'—5' Linkage

The syntheses were carried out in a model 381A DNA synthesizer supplied by Applied Biosystems, Forster City, USA using the 0.2 μmol standard program for all condensation steps. The synthesis cycle is shown above. The support material used was the CPG 10-1400 described in Example 4. The condensations were carried out with the customary nucleoside 3'-phosphites; only in the last reaction cycle were the 3'-O-DMTr-nucleoside 5'-(N,N-diisopropyl-β-cyanoethyl)phosphoramidites described in Example 1 employed. After elimination of the oligonucleotide from the support with concentrated NH$_3$ and removal of all phosphate and base protective groups by heating the solution in ammonia at 60° C. overnight, the sample was desalted by precipitation in ethanol, and the target sequence was purified from shorter fragments by polyacrylamide gel electrophoresis. For our investigations we synthesized an eicosathymidylate with only 3'-5' linkages and one with terminal 3'—3' and 5'—5' linkages. We also selected sequences from the SV40 genome. The following oligonucleotides were synthesized:

dT$_{20}$;

dT$_{20}$(3'—3',5'—5');

SV40TS17: 17-mer, sense sequence from SV40 genome at positions 5159–5176;

5'-AGC TTT GCA AAG ATG GA-3'

SV40TAS17: 17-mer, antisense sequence to SV40TS17;

5'-TCC ATC TTT GCA AAG CT-3'

SV40TAS17(3'—3',5'—5'): 17-mer, antisense sequence to SV40TS17 with a 3'—3' and 5'—5' linkage at the ends;

3'-T(5'—5')CC ATC TTT GCA AAG C(3'—3')T-5'

SV40TS35: 35-mer, sense sequence from the SV40 genome at positions 5142–5176;

5'-AGC TTT GCA AAG ATG GAT AAA GTT TTA AAC AGA AG-3'

SV40TAS35: 35-mer, antisense sequence to SV40TS35;

5'-TCT CTG TTT AAA ACT TTA TCC ATC TTT GCA AAG CT-3'

SV40TAS35(3'—3',5'—5'): 35-mer, antisense sequence to SV40TS35 with a 3'— 3' and 5'—5' linkage at the ends;

3'-T(5'—5')CT CTG TTT AAA ACT TTA TCC ATC TTT GCA AAGC(3'—3')T-5' b) Synthesis of Oligonucleotides with Terminal 3'—3' Linkage

The support material used was the CPG 10-1400 described in Example 4. The condensations were carried out with the customary nucleoside 3'-phosphites. After elimination of the oligonucleotide from the support with concentrated NH$_3$ and removal of all phosphate and base protective groups by heating the solution in ammonia at 60° C. overnight, the sample was desalted by precipitation in ethanol, and the target sequence was purified from shorter fragments by polyacrylamide gel electrophoresis. The following oligonucleotide was synthesized:

SV40TAS17(3'—3'): 17-mer, antisense sequence to SV40TS17 with a 3'—3' linkage at the end;

3'-TCC ATC TTT GCA AAG C(3'—3')T-5' c) Synthesis of Oligonucleotides with Terminal 5'—5' Linkage and 2 Terminal Thiophosphate Residues The support material used was commercially available CPG material which contains 5'-O-dimethoxytritylthymidine bonded via the 3'-hydroxyl group. The condensations were carried out with the customary nucleoside 3'-phosphites; only in the last reaction cycle were the 3'-O-DMTr-nucleoside 5'-(N,N-diisopropyl-β-cyanoethyl)phosphoramidites described in Example 1 employed.

In the first two reaction cycles the customary oxidation with iodine is replaced by oxidation with elemental sulfur (reference W. Stec et al. J.A.C.S. 106, page 6077, 1984). After elimination of the oligonucleotide from the support with concentrated NH$_3$ and removal of all phosphate and base protective groups by heating the solution in ammonia at 60° C. overnight, the sample was desalted by precipitation in ethanol, and the target sequence was purified from shorter fragments by polyacrylamide gel electrophoresis.

The following oligonucleotide was synthesized:

SV40TAS17(5'—5'): 17-mer, antisense sequence to SV40TS17 with a 5'—5' linkage at the 5' end and two thiophosphate internucleotide linkages at the 3' end

3'-T(5'—5')CC ATC TTT GCA AAG(P$_S$) C(P$_S$)T-3'

EXAMPLE 6

Analysis of the Structure and Sequence of an Oligonucleotide with Terminal 3'—3' and 5'—5' Linkage The oligonucleotides were sequenced by the method of Maxam and Gilbert (see M. Maxam and W. Gilbert, Methods in Enzymology 65, 499–560 (1980)). In each case, 100 pmol of the samples were radiolabeled on the 5'-OH group in the presence of (γ-$^{32}$P)-ATP/T4 polynucleotide kinase and subsequently the following base-specific reactions were carried out:

(A+G) reaction: Protonation of the bases by formic acid

G reaction: Reaction with dimethyl sulfate (T+C) reaction: Hydrazinolysis

C reaction: Reaction with hydrazine in the presence of 5M NaCl

The oligonucleotide chains were cleaved at the modified sites by treatment with 1M piperidine at 95° C.; it was possible to fractionate the fragments by polyacrylamide gel electrophoresis (20% acrylamide, 7M urea) and detect them by autoradiography. FIG. 1 shows the autoradiogram of the sequencing of SV40TS17, SV40TAS17 and SV40TAS17 (3'—3',5'—5') (see Example 5 for a description of the oligonucleotides). Since the chains were labeled at the 5'-OH group, the base sequence can be read off in the 3'-5' direction when there are only 3'-5' linkages. As a consequence of the 3'—3' end, however, the oligonucleotide SV40TAS17(3'—3',5'—5') has the radiolabeled 5'-OH group at its 3' terminus; this reverses the direction of reading the sequence (FIG. 1). This is also evidence of the 5'—5' phosphodiester linkage at the 5' terminus of the chain with a free 3'-OH group which cannot be phosphorylated by the enzyme polynucleotide kinase.

EXAMPLE 7

Examination of the Stability of an Oligonucleotide Provided with 3'—3' and 5'—5' Ends in the Blood Serum Test A) Kinasing of an Eicosathymidylate with 3'—3' and 5'—5' Ends Reference: T. Mizuno, M.-Y. Chou and M. Inouye, Proc. Natl. Acad. Sci. USA 81, 1966–1970 (1984)

Mixture: 1 μl of oligonucleotide (0.01 OD$_{260}$)

```
1 µl of 10 × kinase buffer
1 µl of T4 polynucleotide kinase
1 µl of γ-³²P-dATP (specific activity: 6000 Ci/mmol)
6 µl of H₂O
```

The mixture is incubated at 37° C. for 30 min, then stopped by addition of 90 µl of H₂O and fractionated on a ®Sephadex G 50 column. The product fractions are combined and lyophilized.

B) Blood Serum Test

| Reference: | S. M. Heywood, Nucleic Acids Res. 14, 6771–6772 (1986) |
|---|---|
| Mixture: | 0.01 OD$_{260}$ of radiophosphorylated oligonucleotide for the reference |
| | 0.01 OD$_{260}$ T$_{20}$, for the experiment 0.01 OD$_{260}$ T$_{20}$ with 3'-3' and 5'-5'-linked ends |
| | 50 µl of fresh human serum |

The serum is added to each sample and briefly shaken by hand. Then immediately 3 µl are removed by pipette for the 0 value and added to 3 µl of formamide loading buffer in order to stop the enzyme activity. The samples are then incubated at 37° C. For the kinetics, 3 µl are removed after defined intervals of time and stopped as described above.

Reference: 5 min, 8 min, 11 min, 15 min, 30 min

Experiment: 5 min, 8 min, 11 min, 15 min, 30 min, 90 min

The samples are loaded onto a 20% polyacrylamide gel and separated by gel electrophoresis and then autoradiographed.

Figure 2:
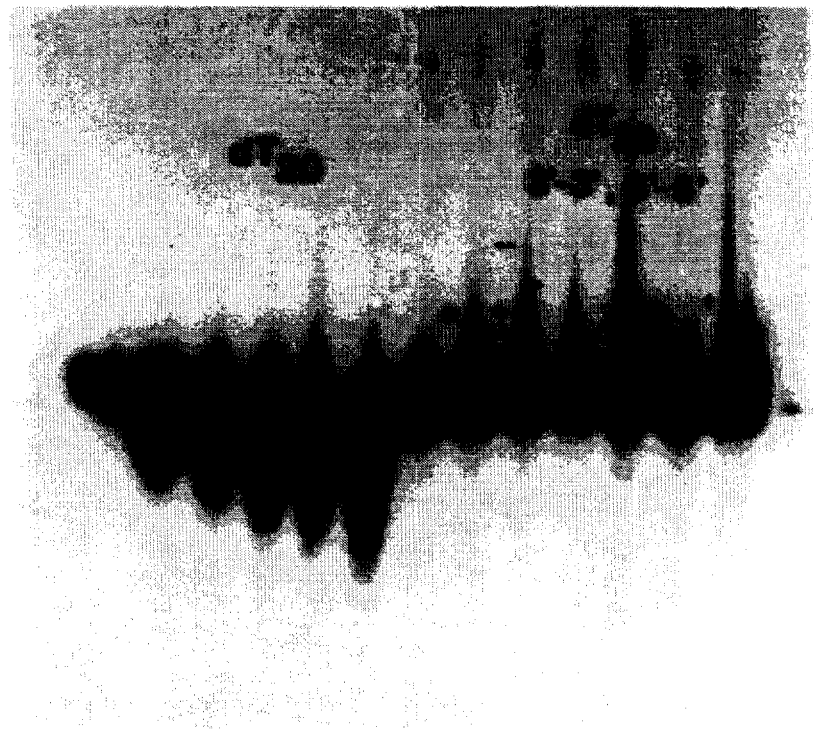
FIG. 2 shows an autoradiogram of the cleavage of $dT_{20}$ and $dT_{20}$ (3'—3', 5'—5') with fresh human serum.

Autoradiogram of the cleavage with fresh human serum from the left (see FIG. 2):

Reference: 0 value, 5 min, 8 min, 11 min, 15 min, 30 min

Experiment: 0 value, 5 min, 8 min, 11 min, 15 min, 30 min, 90 min

It is evident that degradation of the natural oligonucleotide has started after only 5 min. Cleavage increases with increasing time. Even after incubation for 90 minutes the modified oligonucleotide is virtually unchanged. The weak bands which are to be seen at all the kinetic values result from the activity of the endonucleases present in the serum. This cleavage is important for therapeutic use of these oligonucleotides and is desirable because it guarantees the slow degradation of the active substance so that no accumulation of these substances in the body can occur.

EXAMPLE 8

Investigation of the Behavior of Oligonucleotides with Terminal 3'—3' and 5'—5' Linkage Toward Snake Venom Phosphodiesterase A) Kinasing of an Eicosathymidylate with 3'—3' and 5'—5' Ends as Described in Example 7)

B) Hydrolysis of an Eicosathymidylate with 3'—3' and 5'—5' Ends Using Snake Venom Phosphodiesterase

| Reference: | A. Hirashima, S. Sawaki, Y. Inokuchi and M. Inouye, PNAS USA 83, 7726–7730 (1986) |
|---|---|
| Mixture: | 5 µl of RNA carrier |
| | 50 µl of SQ buffer |
| | 1 µl of SVpdE (1.5 u/µl) |

The radiophosphorylated sample (reference: T$_{20}$, experiment: T$_{20}$ with terminal 3'—3' and 5'—5' linkage) is lyophilized, and the RNA carrier and the SQ buffer are added thereto. In each case, 5 µl are removed by pipette from this mixture for the 0 value, and the remainder of the solution is mixed with enzyme and incubated at 37° C. 5 µl samples are taken after 5 min, after 15 min and after 30 min for the reference kinetics, and 5 µl samples are taken after 5 min, 30 min, 45 min, 60 min and 90 min for the kinetics of the eicosathymidylate with 3'—3' and 5'—5' ends. To inactivate the enzyme, the samples are, immediately after removal, heated in a waterbath at 95° C. for 2 min. The samples are lyophilized and loaded onto an analytical 20% polyacrylamide gel. Autoradiography is carried out after the fractionation by gel electrophoresis.

Figure 3:
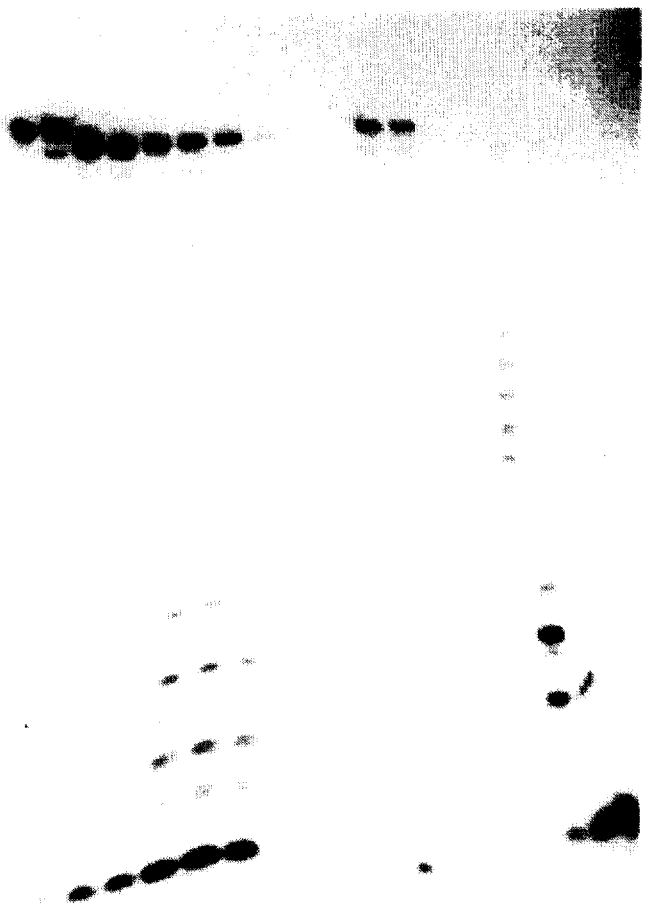
FIG. 3 shows an autoradiogram of the SVpdE cleavage of $dT_{20}$ and $dT_{20}$ (3'—3', 5'—5').

Autoradiogram of the SVpdE cleavage (see FIG. 3):

from the left: T$_{20}$ (reference), T$_{20}$ with terminal 3'—3' and 5'—5' linkages, kinetics of the experiment: after 5 min, 15 min, 30 min, 45 min, 60 min, 90 min, mix of 0 min/15 min, mix of 0 min/30 min, reference kinetics: after 5 min, 15 min, 30 min, 45 min.

The 5'—5' linkage is immediately cleaved as already described. It is a clear indication of the structure that subsequent cleavage takes place only very slowly compared with the reference. Cleavage of the 5'—5'-phosphodiester linkage results in a molecule which has at the cleavage site a 5'-hydroxyl group. The molecule is 5'-phosphorylated at the other terminus. Attack by snake venom phosphodiesterase is impossible at both termini. The slow but very definite subsequent degradation is probably attributable to the presence of a single-strand-specific endonuclease which is described by the manufacturer (J. G. Izant and H. Weintraub, Cell 36, 1007–1015 (1984)) and which converts the supercoiled PM2 DNA into open forms. It is easy to read off the length of the sequence. However, only 19 bands can be read off because the 5'—5'-phosphodiester linkage has already been cleaved at the first kinetic value after 5 min.

EXAMPLE 9

Investigations of the Hybridization Behavior of Oligonucleotides Provided with Terminal 3'—3' and 5'—5' Ends To investigate the hybridization behavior, melting plots were recorded. In each case equimolar amounts (5.23 nmol) of SV40TS17 and SV40TAS17(3'—3',5'—5') (see Example 5 for description of the oligonucleotides) were dissolved in 1 ml of a 10 mM sodium cacodylate/100 mM NaCl buffer, pH 7.0, and heated to 70° C., and the progress of renaturation on slow cooling (1 degree/min) was determined by measuring the absorption of the solution. The reference plot was recorded by using the same amounts of SV40TS17 and SV40TAS17. In each case 4.75 nMol of SV40TS35 and SV40TAS35 or SV40TS35 and SV40TAS35(3'—3',5'—5') were analogously mixed in the buffer and heated to 90° C., and the absorption on cooling was measured. The resulting melting plots yielded the following T$_m$ values:

| SV40TS17 • SV40TAS17 | 54.1° C. |
|---|---|
| SV40TS17 • SV40TAS17(3'-3',5'-5') | 53.3° C. |
| SV40TS35 • SV40TAS35 | 65.5° C. |
| SV40TS35 • SV40TAS35(3'-3',5'-5') | 64.2° C. |

The abiological linkages thus reduce the melting temperatures only by 0.6° for the 17 mer and 1.3° for the 35 mer.

EXAMPLE 10

Inhibition of the Biosynthesis of SV40 T Antigen by Oligonucleotides with Terminal 3'—3' and 5'—5' Linkage A) Cell Culture COS1 cells were cultured in Dulbecco's modified Eagle medium (DMEM) with 10% fetal calf serum. The tissue culture dishes were incubated at 37° C. and 7.5% CO$_2$.

B) Radiolabeling and Cell Disruption

About 4×10⁴-cells were cultured as monolayer in tissue culture dishes. The confluent cell lawn was washed three times with methionine-free DMEM and subsequently labeled with 100 µCi of $^{35}$S-methionine. For the antisense modulation experiments' the cells were incubated simultaneously with the oligonucleotide SV40TAS17(3'—3',5'—5') and radioactive methionine at 37° C. for 30 min. Subsequently the cells were washed twice with DMEM which contained 10% fetal calf serum and unlabeled methionine, and left in this medium for a further 30 min. To disrupt the cells they were treated with ice-cold phosphate-buffered saline (PBS), scraped off the dishes and centrifuged at 400 g for 2 min. The cell pellet was then lyzed with 0.4 ml of disruption buffer (0.5% Nonidet P40, 100 mM tris-HCl, pH 9.0, 0.1M NaCl) per 3×10⁶ cells on ice for 45 min. To prevent proteolysis, 1% Trasylol and phenylmethylsulfonyl fluoride were added to a final concentration of 0.25 mg/ml to the disruption buffer. The lysate was then centrifuged in an ultracentrifuge (105.000 g) at 4° C. for 30 min until clear. A 10 µl aliquot was removed and the protein content was measured by the Lowry method. Identical amounts of total protein were employed for the immunoprecipitation.

C) Immunoprecipitation

The monoclonal antibody PAb108 was used for the immunoprecipitation both of SV40 wild-type T antigen and of the mutant T antigen localized in the cytoplasm. The antibody was purified from the hybridoma supernatant by chromatography on protein A-Sepharose. The cell extract was preprecipitated with 100 µl of a 10% strength suspension of heat-inactivated and formaldehyde-fixed bacteria of the strain *Staphylococcus aureus* (Cowan 1) at 4° C. overnight. The bacteria were then removed by centrifugation, the supernatant was incubated with the monoclonal antibody at 4° C. for at least 2 hours, and the highly specific immune complexes were formed by adding *S. aureus*. This procedure was repeated up to 3 times in order to ensure complete precipitation. The immunoprecipitates were then washed as follows: three times with 50 mM Tris-HCl, pH 8.0, 500 mM LiCl, 1 mM DTT, 1 mM EDTA, 1% Trasylol; twice with 50 mM Tris-HCl, pH 7.4, 0.15M NaCl, 5 mM EDTA, 1% Nonidet P40 and once with 50 mM NH₄HCO₃. They were then eluted with 200 µl of elution buffer (50 mM NH₄HCO₃, 1% SDS, 1% β-mercaptoethanol) at 4° C. for 45 min, lyophilized, dissolved by boiling for 10 minutes in 20 µl of sample buffer (65 mM Tris-HCl, pH 6.8, 5% β-mercaptoethanol, 1% glycerol, 0.01% bromophenol blue) and loaded onto a 3% polyacrylamide gel (10% SDS). The proteins were fractionated by discontinuous gel electrophoresis; it was possible to localize the bands by fluorography on X-ray film (Kodak X-AR).

A 70% inhibition of virus growth was recorded with oligonucleotides which were prepared according to the invention in such a way that they spanned the start of translation of the T antigen, when an extracellular concentration of 30 µmolar was used. This contrasts with the activity of the corresponding sequences which were not synthesized according to the invention, that is to say without 3'—3' and 5'—5' linkages. In this case no inhibition was detectable when the same concentration was used.

Figure 4:
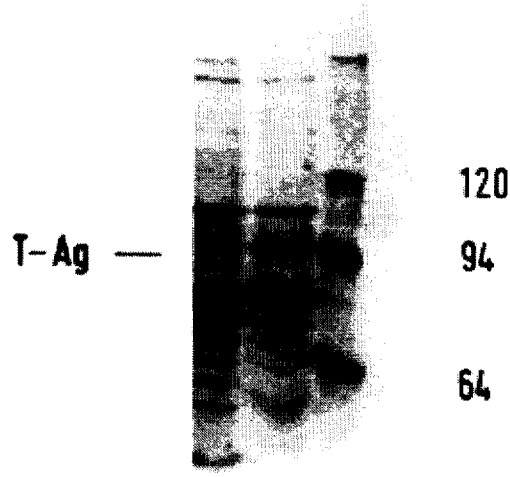
FIG. 4 shows inhibition of T-Ag expression by antisense oligonucleotides.

FIG. 4 shows a distinct inhibition of T Ag biosynthesis on treatment of the cells with 30 µM SV40TAS17(3'—3',5'—5').

EXAMPLE 11

Examination of the Stability of Oligonucleotides Modified at Just One End by a 3'3' or 5'5' Inverted Phosphodiester Linkage Oligonucleotides are degraded by nucleases primarily from their 3'-terminus (J. P. Shaw, K. Kent, J. Bird, J. Fischbach, B. Froehler, Nucleic Acids Res. 19, 747-750 (1991)). The following investigation served the purpose to show if merely one 3'3'-terminal phosphodiester linkage is sufficient to stabilize the oligonucleotide against rapid degradation in blood serum. Since a $^{32}$P-labelled phosphate residue is removed by phosphatases in serum on prolonged treatment, a fluorescein label was used for detection.

The following oligonucleotide sequences from *Xenopus levis* were synthesized for investigation of their stability:

Xelev 1: 3'-A(5'5')GC CTC AAA C*AT GTG TGA CG 3'
Xelev 2: 5' AGC CTC AAA C*AT GTG TGA C(3'3')G 5'

Synthesis of oligonucleotides has been performed as described in Example 5 except that in the 10th coupling reaction a base-modified Cytidin-phosphoramidite C* was used to allow for a subsequent covalent attachment of the fluorescein label. Introduction of fluorescein has been accomplished according to the protocol of the commerical supplier (Pharmacia LKB Biotechnology, Auto Primer™ Synthesis Kit Instructions (XYA-023-00-01)). The modified oligonucleotides were purified by polyacrylamide-gel electrophoresis.

| Serum assay: | 10 pMol oligonucleotide 140 µl human serum |
|---|---|

The samples were incubated at 37° C. After 15, 30, 45 and 60 minutes, 8 hrs and 72 hrs, aliquotes of 20 µl were taken, extracted two times with phenol/chloroform/isoamylalcohol (25:24:1, v:v:v) and finally the oligonucleotides were precipitated with alcohol. The cleavage products were separated on a 16% polyacrylamide gel by means of the automatic sequenator ®A.L.F. (Pharmacia, Freiburg). As can be seen from FIG. 5 is the stability of Xelev 1 with just one inverted phosphodiester linkage at the 5'-end rather low in that on serum treatment after 15 minutes already cleavage products appear, after 60 minutes the oligonucleotide is almost completely degraded. On the opposite, the oligonucleotide Xelev 2 provided with just one 3'3'-phosphodiester linkage at the end is only partially degraded even after 72 hours treatment.

EXAMPLE 12

Inhibition of p53 Gene Expression in an In Vitro Translation System

In order to quantify inhibition of protein biosynthesis in a cell-free system by modified oligonucleotides we investigated their impact on the translation of p53 mRNA (E. Reihsaus), M. Kohler, S. Kreiss, M. Oren, M. Montenarh, Oncogene 5, 137–144 (1990)).

The following antisense oligonucleotide which is directed against the translational start region of p53-mRNA has been synthesized:

5' H₂N(CH₂)₆ p TAA TCA GTC GTT GTT CCA CAC CTT (3'3') T

As a control we used the sense sequence:

5' H₂N(CH₂)₆ p AAA GGT GTG GAC CAA CGA CTG ATT (3'3') A

Protein biosynthesis of p53 has been investigated

| | |
|---|---|
| 1. | without any addition of oligonucleotide |
| 2. | after addition of 30 μM sense oligonucleotide (control) |
| 3. | after addition of 1 μM antisense oligonucleotide |
| 4. | after addition of 10 μM antisense oligonucleotide |

Quantification was achieved by densiometric determination of the stained protein bands on a protein gel. FIG. 6 shows that addition of 10 μM of the antisense oligonucleotide to the in vitro protein biosynthesis system results in a 70% inhibition whereas on addition of only 1 μM almost no inhibition could be detected. Addition of the sense oligonucleotide which does not bind to p53 mRNA did not result in inhibition of p53 biosynthesis even at a concentration as high as 30 μM.

We claim:

1. An oligodeoxynucleotide of the formula I or II

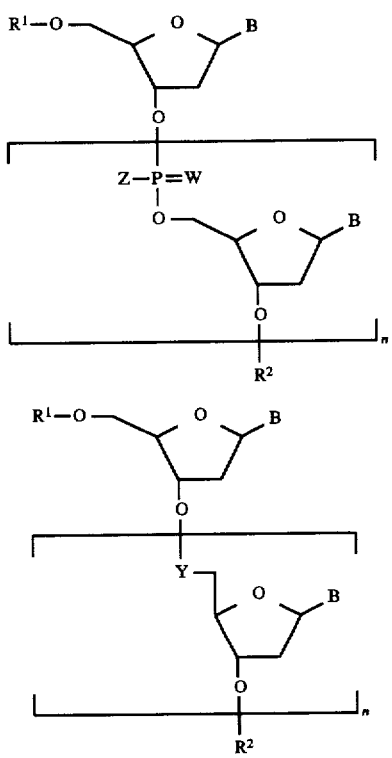

in which $R^1$ is hydrogen or a radical of formula III

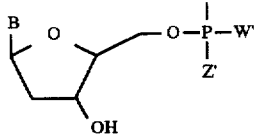

$R^2$ is a radical of the formula IV

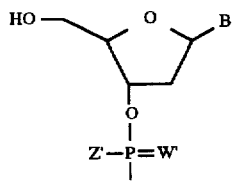

B is a base selected from adenine, thymine, cytosine, guanine, purine, 2,6-diaminopurine, 7-deazaadenine, 7-deazaguanine and $N^4,N^4$-ethenocytosine;

W and W' are independently of one another, oxygen or sulfur;

Z and Z' are, independently of one another, $O^-$; $S^-$; $C_1$–$C_{18}$-alkoxy; $C_1$–$C_{18}$-alkyl; $NHR^3$ with $R^3$=$C_1$–$C_{18}$-alkyl, or $C_1$–$C_4$-alkoxy-$C_1$–$C_6$-alkyl; $NR^3R^4$ in which $R^3$ is as defined above and $R^4$ is $C_1$–$C_{18}$-alkyl, or in which $R^3$ and $R^4$ form, together with the nitrogen atom carrying them, a 5–6-membered heterocyclic ring which can additionally contain another hetero atom from the series comprising O, S, N;

Y is a radical from the series comprising O—Si(R)$_2$, OCH$_2$, C(O)NR or O—CH$_2$—C(O) in which R is $C_1$–$C_6$-alkyl, aryl or $C_5$- or $C_6$-cycloalkyl; and n is an integer from 10–40;

or a physiologically tolerated salt thereof.

2. The oligodeoxynucleotide of the formula I as claimed in claim 1, in which $R^2$ is a radical of the formula IV and $R^1$ is hydrogen; or $R^1$ and $R^2$ are a radical of the formulae III and IV respectively where either W or Z is not oxygen.

3. An oligonucleotide of the formula I as claimed in claim 1, wherein W is oxygen or both Z and W are oxygen.

4. An oligonucleotide of the formula I as claimed in claim 1, wherein $R^2$ is a radical of the formula IV, and $R^1$ is hydrogen.

5. The oligodeoxynucleotide of the formula I or II as claimed in claim 1, which is additionally substituted by a substituent selected from the group consisting of an alkyl radical with up to eighteen carbon atoms, cholesteryl, and bile acid.

6. The oligodeoxynucleotide of the formula I or II as claimed in claim 1, wherein n is an integer from 15–25.

7. The oligodeoxynucleotide of the formula I or II as claimed in claim 1, wherein Z and Z' are, independently of one another, $C_1$–$C_8$-alkoxy; $C_1$–$C_8$-alkyl; $NHR^3$ with $R^3$=$C_1$–$C_8$-alkyl, or methoxyethyl; or $NR^3R^4$ in which $R^3$ is as defined in claim 1 and $R^4$ is $C_1$–$C_8$-alkyl.

8. The oligodeoxynucleotide of the formula I or II as claimed in claim 1, wherein Z and Z' are, independently of one another, $C_1$–$C_3$-alkoxy; $C_1$–$C_3$-alkyl; $NHR^3$ with $R^3$=$C_1$–$C_4$-alkyl; or $NR^3R^4$ in which $R^3$ is as defined in claim 1 and $R^4$ is $C_1$–$C_4$-alkyl.

9. The oligodeoxynucleotide of the formula I or II as claimed in claim 1, wherein Z and Z' are, independently of one another, methoxy or methyl.

10. The oligodeoxynucleotide of the formula I or II as claimed in claim 1, wherein Z and Z' are, independently of one another, $NR^3R^4$ in which $R^3$ and $R^4$ form, together with the nitrogen atom carrying them, N-morpholinyl.

* * * * *

UNITED STATES PATENT AND TRADEMARK OFFICE
CERTIFICATE OF CORRECTION

PATENT NO. : 5,750,669
DATED : May 12, 1998
INVENTOR(S) : Rösch et al.

It is certified that error appears in the above-identified patent and that said Letters Patent is hereby corrected as shown below:

In Claim 1, Column 27, line 35, after "radical of", insert --the--.

In Claim 1, Column 27, line 37, in the formula (III),

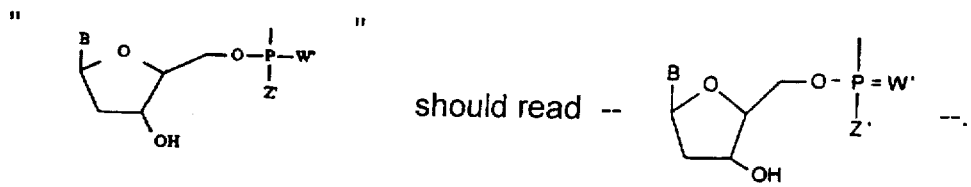

In Claim 1, Column 28, line 4, after "are" insert --,--.

In Claim 3, Column 28, line 22, "oligonucleotide" should read --oligodeoxynucleotide--.

In Claim 4, Column 28, line 24, "oligonucleotide" should read --oligodeoxynucleotide--.

Signed and Sealed this

Sixth Day of July, 1999

Attest:

Attesting Officer

Q. TODD DICKINSON

Acting Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

AGCTTTGCAA AGATGGA                                    17

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TCCATCTTTG CAAAGCT                                    17

( 2 ) INFORMATION FOR SEQ ID NO:3:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

AGCTTTGCAA AGATGGATAA AGTTTTAAAC AGAAG                35

( 2 ) INFORMATION FOR SEQ ID NO:4:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

TCTCTGTTTA AAACTTTATC CATCTTTGCA AAGCT                35